(12) United States Patent
Feldkhun et al.

(10) Patent No.: US 8,558,998 B2
(45) Date of Patent: Oct. 15, 2013

(54) FOURIER DOMAIN SENSING

(75) Inventors: Daniel Feldkhun, Boulder, CO (US);
Kelvin H. Wagner, Boulder, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 178 days.

(21) Appl. No.: 13/247,610

(22) Filed: Sep. 28, 2011

(65) Prior Publication Data

US 2012/0257197 A1    Oct. 11, 2012

Related U.S. Application Data

(63) Continuation-in-part of application No. 12/485,858, filed on Jun. 16, 2009, now Pat. No. 8,184,279.

(60) Provisional application No. 61/387,443, filed on Sep. 28, 2010, provisional application No. 61/061,745, filed on Jun. 16, 2008.

(51) Int. Cl.
*G01J 1/36* (2006.01)

(52) U.S. Cl.
USPC ........... 356/217; 356/432; 356/300; 250/351; 382/206; 382/232; 382/254

(58) Field of Classification Search
USPC ........... 356/300, 217, 432; 250/351; 382/206, 382/232, 254, 280
See application file for complete search history.

(56) References Cited

U.S. PATENT DOCUMENTS

| | | | |
|---|---|---|---|
| 3,599,147 A | 8/1971 | Rogers et al. | |
| 4,717,916 A | 1/1988 | Adams et al. | |
| 5,099,681 A | 3/1992 | Dils | |
| 6,016,196 A | 1/2000 | Mermelstein | |
| 6,255,642 B1 | 7/2001 | Cragg et al. | |
| 2005/0058352 A1 | 3/2005 | Deliwala | |
| 2006/0077553 A1 | 4/2006 | Neilson | |
| 2008/0260014 A1 | 10/2008 | Yang et al. | |
| 2009/0141995 A1 | 6/2009 | Chakraborty et al. | |
| 2009/0257464 A1 | 10/2009 | Dantus et al. | |
| 2009/0316141 A1 | 12/2009 | Feldkhun | |
| 2010/0001727 A1 | 1/2010 | Frydman et al. | |
| 2010/0207037 A1 | 8/2010 | Tearney et al. | |
| 2010/0214404 A1 | 8/2010 | Chen et al. | |
| 2011/0149298 A1 | 6/2011 | Arieli et al. | |

FOREIGN PATENT DOCUMENTS

WO    2009147425 A1    12/2009

OTHER PUBLICATIONS

Hoffman et al. Breaking the Diffraction Barrier in Fluorescence Microscopy At Low Light Intensities by Using Reversibly Photoswitchable Proteins. www.pinas.org/cgi/doi/10.1073/pnas.0506010102 pp. 17565-17569. vol. 102, No. 49. Dec. 6, 2005.

Feldkuhn et al. Fourier Analysis and Synthesis Tomography. Report prepared by Michael B. Sinclair. Sandia National Laboratories. 28 pages. May 2010.

The Regents of the University of Colorado, A Body Corporate. Notification of Transmittal of the International Search Report and the Written Opinion of the International Searching Authority, or the Declaration. International Application No. PCT/US11/53719. International Filing Date: Sep. 28, 2011.

*Primary Examiner* — Layla Lauchman
(74) *Attorney, Agent, or Firm* — Marsh Fischmann & Breyfogle LLP; Daniel J. Sherwinter

(57) ABSTRACT

Methods and systems are disclosed of sensing an object. A first radiation is spatially modulated to generate a structured second radiation. The object is illuminated with the structured second radiation such that the object produces a third radiation in response. Apart from any spatially dependent delay, a time variation of the third radiation is spatially independent. With a single-element detector, a portion of the third radiation is detected from locations on the object simultaneously. At least one characteristic of a sinusoidal spatial Fourier-transform component of the object is estimated from a time-varying signal from the detected portion of the third radiation.

40 Claims, 29 Drawing Sheets

FOURIER DOMAIN SENSING

CROSS-REFERENCE TO RELATED APPLICATIONS

This application is a nonprovisional of, and claims the benefit of the filing date of, U.S. Prov. Pat. Appl. No. 61/387,443, filed Sep. 28, 2010, the entire disclosure of which is incorporated herein by reference for all purposes. This application is also a continuation-in-part of U.S. patent application Ser. No. 12/485,858 ("the parent application"), filed Jun. 16, 2009, the entire disclosure of which is also incorporated herein by reference for all purposes. The parent application is a nonprovisional of, and claims the benefit of the filing date of, U.S. Prov. Pat. Appl. No. 61/061,745, filed Jun. 16, 2008, the entire disclosure of which is incorporated herein by reference for all purposes.

STATEMENT REGARDING FEDERALLY SPONSORED RESEARCH OR DEVELOPMENT

This invention was made with government support under grant number NNX08AM97G awarded by NASA. The government has certain rights in the invention.

BACKGROUND OF THE INVENTION

The present invention relates to the fields of image sensing and microscopy, and more specifically to methods, systems, and apparatuses for measuring the spatial frequency spectrum of an object using dynamic interference patterns.

Wide-field lens-based imaging systems form images by causing light diffracted or emitted by the object to interfere on a resolving detector or multi-element detector array. From the perspective of Fourier optics, the object may be considered as a coherent sum of sinusoidal Fourier components, such that the angle of light diffracted or emitted by each Fourier component varies with may be proportional to its spatial frequency. Because the optical system can collect only a cone of light defined by its numerical aperture (NA), off-axis light that carries high spatial frequency information may be rejected, thereby limiting spatial resolution. Wavefront aberrations in the optical path may further reduce resolution. Moreover, because the depth of field (DOF) of lens-based imaging systems typically has an inverse quadratic dependence on the NA, high-resolution imaging systems can maintain focus within a very limited depth range, typically only a few wavelengths. Furthermore, due to the challenges of manufacturing large, high NA, high-precision optics, the objective lens is typically be located within a working distance (WD) of only a few millimeters from the object in high-resolution microscopes.

Super-resolution wide-field microscopy techniques in the literature often exploit structured illumination in conjunction with a lens-based imaging system in order to surpass the diffraction resolution limit. Such techniques typically process a sequence of images acquired as the object is illuminated with multiple patterns, such as phase-shifted sinusoids, thereby effectively down-converting high-frequency Fourier components to lower spatial frequencies via the Moire effect. This approach is generally be subject to the same NA-dependent limit on DOF and WD as conventional imaging systems and trades imaging speed for gain in resolution.

Extending the lateral resolution limit even further, U.S. Pat. No. 6,255,642, incorporated herein by reference, may describe the use of an evanescent field produced by standing wave illumination due to total internal reflection at an interface with a transparent optical material in order to perform super-resolution imaging in the near-field. U.S. Pat. Nos. 5,394,268 and 6,055,097, incorporated herein by reference, may describe related structured illumination imaging techniques wherein the object is illuminated with interference patterns directed along the optical axis to reduce the effective DOF of the system, which may enable sub-wavelength axial sectioning.

On the other hand, lensless projection and diffraction tomography techniques may be used for high-resolution imaging of two-dimensional and three-dimensional structures by directly measuring the angular distribution of radiation transmitted or diffracted by an object, and are often used in wavelength regimes, such as X-rays, where lens-based optical imaging is challenging. These techniques typically rely on multiple radiation sources and detectors to measure Fourier components of the object along distinct paths in Fourier space, and a number of methods have been developed for reconstructing two- and three-dimensional images from such tomographic measurements, including the widely-used Filtered Backprojection algorithm.

A structured illumination remote sensing approach, called Fourier Telescopy, has been proposed (see Ustinov, N. D. et al., Sov. J. Quantum Electron. 17, 108-110 (1987), incorporated herein by reference) wherein the object is illuminated with one or more sinusoidal interference patterns that may be generated by an array of radiation sources and the response from the object is recorded with a single-element non-resolving detector to measure one or more Fourier components of a remote object.

U.S. Pat. No. 4,584,484, incorporated herein by reference, may describe a technique wherein an object is illuminated with a moving interference pattern produced by a pair of laser beams. In this technique, light transmitted by the object in response to the illumination is recorded as the angular separation or wavelength of the illuminating beams is mechanically scanned using an arrangement of mirrors during the motion of the pattern, thereby measuring the object's complex spatial Fourier transform along a direction. Additional "Fourier slices" may be acquired by rotating the illumination with respect to the object. An image may be synthesized by Fourier-transforming the acquired data.

U.S. Pat. Nos. 5,384,573 and 5,751,243, incorporated herein by reference, may describe an optical imager similar in principle to Synthetic Aperture Radar, where coherently scattered radiation from the object is detected as the optical plane orientation and the angular separation between an illumination beam and the line of sight of a single-element detector are varied. An optical heterodyne Fourier processor may be used to sequentially synthesize the image.

There is thus a need for tools and techniques that may not be limited to sequential sampling of Fourier components along a direction. Furthermore, there is a need for tools and techniques that may not rely on interference of discrete beams of radiation. Moreover, there is a need for tools and techniques that may provide a flexible, programmable means for measuring a variety of distributions of Fourier components in two and three-dimensional Fourier space through real-time electronic control. In addition, there is a need for tools and techniques that may provide for high speed one, two, and/or three dimensional image acquisition and synthesis.

SUMMARY

Embodiments of the invention provide methods of sensing an object. A first radiation is spatially modulated to generate a structured second radiation. The object is illuminated with the structured second radiation such that the object produces a third radiation in response. Apart from any spatially dependent delay (which may or may not exist), the third radiation has a time variation that is substantially spatially independent. With a single-element detector, a portion of the third radiation is detected from a plurality of locations on the object substantially simultaneously. At least one characteristic of one or more sinusoidal spatial Fourier-transform components of the object is estimated from a time-varying signal from the detected portion of the third radiation.

In some embodiments, the first radiation is spatially modulated by propagating a traveling modulation pattern along a direction. A plane-wave component of the second radiation is diffracted and a Doppler frequency shift is imparted on the plane-wave component. The second radiation may comprise a plurality of plane-wave components, with each distinct pair of the plane-wave components interfering to produce a traveling sinusoidal excitation pattern component probing one or more harmonic spatial Fourier-transform components of the object and contributing a time-varying detector signal comprising one or more frequencies corresponding to an integer multiple of a temporal frequency difference of the each distinct pair of plane-wave components and having zero or non-zero frequency offset.

The traveling modulation pattern may be produced using one or more acousto-optic devices comprising at least one of a Bragg cell or a surface-acoustic-wave optical modulator. Each of the acousto-optic devices may be controlled with an electrical drive signal, with each frequency component of the electrical drive signal or an intermodulation thereof imparting a harmonic Doppler frequency shift to one of the plane-wave components of the second radiation.

The first radiation may be spatially demodulated by spatially modulating the first radiation along a plurality of non-parallel directions. The acousto-optic devices may comprise at least one of a multidimensional acousto-optic device or a plurality of non-collinear acousto-optic devices arranged in tandem in close proximity to each other or in conjugate optical planes. The drive signals may comprise an array of frequencies, with at least one pair of frequencies resulting in a distinct tone in the time-varying detector signal that measures a distinct component of a three-dimensional Fourier transform of the object. For example, the electrical drive signal may comprise a non-redundant array of frequencies.

In other embodiments where the second radiation comprises a plurality of plane-wave components, a difference between temporal frequencies of each pair of plane-wave components is substantially distinct from temporal frequency differences of other pairs of plane-wave components that produce distinct sinusoidal excitation patterns.

The characteristic of the sinusoidal spatial Fourier-transform components of the object may be estimated by obtaining substantially simultaneous measurements of one or more distinct spatial Fourier-transform components of the object from the signal by Fourier analysis.

In some embodiments, a response by the object to the second radiation is nonlinear, and a portion of the time-varying signal due to a sinusoidal excitation pattern component comprises harmonic temporal frequencies measuring harmonic spatial Fourier-transform components. The response may be due to saturable fluorescence in one embodiment and in another may be due to depletion of fluorescence using an auxiliary depletion illumination pattern traveling substantially in unison with the traveling sinusoidal excitation pattern but operating at a substantially distinct wavelength. In some instances, the response is coherent.

The second radiation may have a spectral distribution, with a width of the spectral distribution being controlled to set a depth of field of the sensing. A group delay dispersion of the first radiation may also be controlled to set a focal plane for the sensing.

When the first and second radiations have a spectral distribution, wavelengths of the first radiation may be angularly spectrally dispersed to maintain an extended depth of field, with depth of field and resolution being decoupled. In some instances, the first radiation has a partial spatial coherence, which may be controlled to set a depth of field of the sensing.

In other embodiments where the second radiation has a spectral distribution, limited coherence of the first radiation may result in portions of the time-varying signal due to illumination that is scattered at least once before impinging on the object being suppressed relative to portions of the time-varying signal due to illumination not thus scattered, resulting in increased measurement contrast and extended measurement depth within or behind a scattering medium. The scattering medium may comprise biological tissue, and the third radiation may be fluoresced by a component of the biological tissue in response to the illumination.

The third radiation may be due to at least one of multiphoton fluorescence, harmonic generation, coherent nonlinear frequency mixing, or Raman scattering. In some such instances, the object may be illuminated with a fourth radiation. The fourth radiation may comprise a counter-propagating pulsed radiation having a different spectrum from the second radiation. The second radiation may be pulsed. The third radiation may be spectrally filtered. The time-varying signal is thereby detected only when the second and fourth radiation pulses overlap in time and space to produce emission with a spectrum distinct from the spectra of the second and fourth radiations. In one embodiment, a relative timing of pulses of the second and fourth radiations is adjusted to control an axial location of overlap of such pulses, thereby providing axial sectioning.

The second radiation may pass through a high-index medium having a higher index of refraction than a sample medium and may form an evanescent field pattern extending into the sample medium at an interface between the high-index medium and the sample medium. The object may be located substantially adjacent to the interface such that it is at least partially within the evanescent field pattern.

The sinusoidal spatial Fourier-transform components of the object may have a substantially sparse and approximately random distribution in the Fourier domain, with the methods further comprising application of a compressed sensing algorithm utilizing minimization of a norm to synthesize a one-dimensional or multi-dimensional image or a transform of such image.

In some embodiments, compensation for errors in a wavefront of the structured second radiation may be compensated while or after estimating the characteristic. For example, the characteristic may comprise phase, with compensation for errors in the wavefront of the structured second radiation comprising formation of closure phases from the estimated Fourier phases. In embodiments where the single-element detector comprises a plurality of detectors and the second and third radiations each have a spectral distribution, the third portion of the radiation may be detected by separately sensing distinct wavelength ranges. At least two of such separate sensings detect a portion of the third radiation due to the same Fourier component of the object. Errors in the wavefront of the structured second radiation are thus compensated for by using signals from the separate sensings.

When the object is located at a distance, an optical surface with coarse phase errors may sometimes be used to illuminate the object with the structured second radiation. The coarse phase errors of the optical surface may be compensated for by making adjustments to at least one of the phase of the sinusoidal components of the structured illumination or the phase of the measured spatial Fourier-transform components of the object.

In one embodiment, the time-varying signal has a carrier frequency, with the method further comprising demodulation of the time-varying signal from the carrier by application of a Hilbert transform to obtain an analytic signal and subtraction of a carrier phase function from the analytic signal. When the time-varying signal has a carrier frequency, another embodiment comprises demodulation of the time-varying signal from the carrier by down-converting and bandpass-filtering a Fourier transform of the detected signal.

In a further embodiment in which the single-element detector comprises a plurality of detectors, with each detector having a distinct wavelength range, the second radiation may have a centrosymmetric position-dependent wavelength distribution substantially near a Fourier-transform optical plane of the spatial modulation.

In other embodiments, methods are provided for measuring one or more sinusoidal spatial Fourier-transform components of an object. The object is illuminated with a first probing radiation comprising one or more plane-wave components having distinct directions of propagation, with the object producing a second radiation in response to the illumination. A distinct frequency shift is imparted on each of the probing radiation components. With a single-element detector, a third reference radiation substantially coherent with respect to the first probing radiation and a portion of the second radiation are detected from a plurality of locations on the object substantially simultaneously. At least one characteristic of the one or more sinusoidal spatial Fourier-transform components of the object is estimated based on a time-varying signal from the detected portion of the second and third radiations.

In some such embodiments, the object comprises phase structure, and a portion of the second radiation is due to coherent scattering of the first and second radiations by the phase structure. The distinct frequency shift may be imparted on the second radiation components by utilizing at least one of a one-dimensional acousto-optic Bragg cell, a multi-dimensional acousto-optic Bragg cell, a surface-acoustic-wave optical modulator, a programmable grating device, a liquid crystal array, or a digital micromirror device.

Methods are also provided for measuring one or more plane-wave components of a first radiation. A single-element detector is illuminated with the first radiation and with a second radiation substantially coherent with respect to the first radiation, the second radiation comprising one or more plane-wave components having distinct directions of propagation. A distinct frequency shift is imparted on each of the second radiation components. The first and second radiations are detected with the detector substantially simultaneously. At least one of amplitude, phase, or direction of propagation of the one or more plane-wave components of the first radiation is estimated based on a time-varying signal due to the detected radiations. The distinct frequency shift may be imparted on the second radiation components by utilizing one of a one-dimensional acousto-optic Bragg cell, a multi-dimensional acousto-optic Bragg cell, a surface-acoustic-wave optical modulator, a programmable grating device, a liquid crystal array, or a digital micromirror device.

In further embodiments, a method is provided for measuring one or more sinusoidal spatial Fourier-transform components of a portion of an image formed by a first radiation. A structured third radiation is generated by spatially modulating a second radiation. A single-element multiphoton detector is illuminated with the structured third radiation and with the first-radiation image portion. The first and third radiations are detected with the multiphoton detector substantially simultaneously. A characteristic of the one or more sinusoidal spatial Fourier-transform components of the portion of the image are estimated based on a time-varying signal due to the detected radiations. The second radiation may use at least one of a one-dimensional acousto-optic Bragg cell, a multi-dimensional acousto-optic Bragg cell, a surface-acoustic-wave optical modulator, a programmable grating device, a liquid crystal array, or a digital micromirror device.

In another embodiment, a method is provided for measuring a sinusoidal spatial Fourier-transform component of a portion of an image formed by a first radiation. An amplitude of the portion of the image is spatially modulated with a traveling modulation pattern to form a structured second radiation. A portion of the structured second radiation is detected from a plurality of locations on the image substantially simultaneously. A characteristic of the sinusoidal spatial Fourier transform component of the portion of the image is estimated based on a time-varying signal due to the detected radiation.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a hyphen and a second label or third label that distinguishes among the similar components. The second or third label may also be used merely to distinguish components that are part of different figures. If the first reference label is used in the specification, the description is applicable to any one of the similar components having the same first reference label irrespective of the second reference or third labels.

DETAILED DESCRIPTION OF EXEMPLARY EMBODIMENTS

This description provides example embodiments only, and is not intended to limit the scope, applicability, or configuration of the invention. Rather, the ensuing description of the embodiments will provide those skilled in the art with an enabling description for implementing embodiments of the invention. Various changes may be made in the function and arrangement of elements without departing from the spirit and scope of the invention.

Thus, various embodiments may omit, substitute, or add various procedures or components as appropriate. For instance, it should be appreciated that in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner.

It should also be appreciated that the following systems, methods, and software may individually or collectively be components of a larger system, wherein other procedures may take precedence over or otherwise modify their application. Also, a number of steps may be required before, after, or concurrently with the following embodiments.

Figure 1:
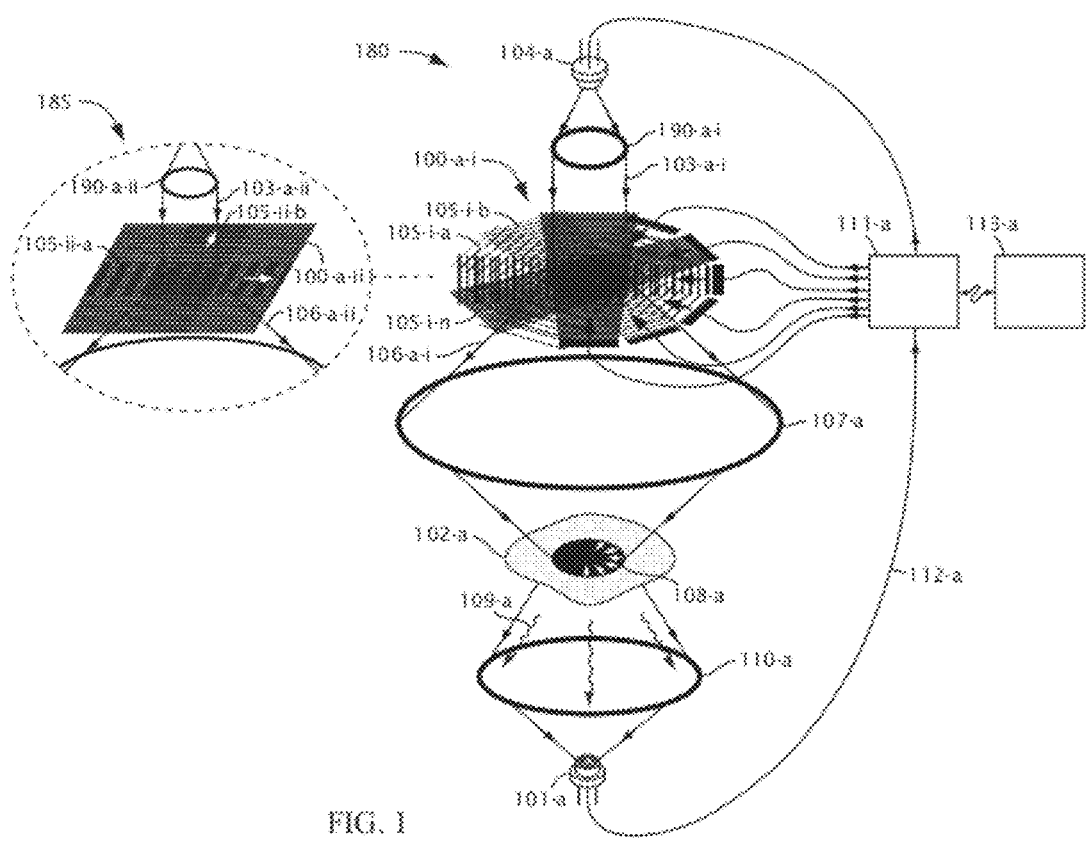
FIG. 1 illustrates a system where an object may be illuminated with a radiation wavefront that has been spatially modulated in two-dimensions using multiple moving sinusoidal patterns and radiation transmitted by the object in response to the illumination is detected with a single-element detector, in accordance with various embodiments.

FIG. 1 illustrates a Fourier domain sensing system 180, in accordance with various embodiments. By using a two-dimensional spatial illumination modulator 100-*a*, the system 180 makes it possible to measure multiple complex Fourier components of the object along multiple dimensions simultaneously using a single-element detector 101-*a*. This data may be used to measure a characteristic of the object 102-*a*, such as its position, shape, or orientation, to classify the object, or to reconstruct an image of the object, merely by way of example. The system may provide, without limitation, parallel high-speed data acquisition without moving components, flexible and configurable Fourier domain sampling, high dynamic range sensing using a single-element detector, simplicity, and/or compatibility with existing spatial light modulator technologies.

In some embodiments, radiation 103-*a*-*i* emitted by a radiation source 104-*a* may be modulated in phase, amplitude, wavelength, and/or polarization using a two-dimensional spatial modulator 100-*a* that may be programmed with a dynamic pattern that can be considered as a combination of moving sinusoidal components 105-*i*-*a*, 105-*i*-*b*, . . . , 105-*i*-*n*. In some embodiments, a lens 190-*a*-*i* may collimate radiation 103-*a*-*i*. In the case of polarization modulation, a polarization analyzing element may be used to convert polarization modulation to intensity modulation. The spatially modulated illumination 106-*a* may then be projected onto the object 102-*a* using a projection optical system 107-*a*, such as a lens, thereby illuminating the object 102-*a* with a combination of dynamic sinusoidal patterns 108-*a*. Radiation 109-*a* scattered, reflected, transmitted, generated, and/or fluoresced by the object 102-*a* in response to the structured illumination 108-*a* may be collected over a substantial range of angles using a detection optical system 110-*a*, such as a lens, onto a single-element detector 101-*a*. An electronic control system 111-*a* may be used to program the spatial modulator 100-*a*, acquire a time-varying detector signal, and/or optionally amplitude-modulate the radiation source 104-*a* in order to convert the time-varying detector signal 112-*a* to a more accessible range of frequencies. A processor and/or computational device 113-*a* in communication with the control system 111-*a* may be used to process the acquired detector signal to compute the Fourier components of the object. The computed Fourier components of the object may be used for a wide variety of purposes including, but not limited to using this information to characterize the object 102-*a* and/or reconstruct its image, as is discussed in more detail below.

In some embodiments, each moving sinusoidal component 105-*i*-*a*, 105-*i*-*b*, . . . , 105-*i*-*n* present in the dynamic spatial modulation pattern may be characterized by a unique combination of spatial frequency, amplitude, spatial phase, direction, and/or equation of motion, and may produce a corresponding moving sinusoidal illumination component at the object with a linearly-related set of characteristics. In one embodiment, each such illumination component may vary sinusoidally in intensity and may move with a constant velocity across the object. By representing the intensity response of the object as an integral sum of its Fourier components, multiplying by the moving sinusoidal intensity pattern, and spatially integrating, a detector signal may be written as the following Equation 1:

$$I_d(t) = I_i \left[ \int\int_{-\infty}^{\infty} A_r(f_x, f_y) e^{j2\pi(f_x x + f_y y)} df_x df_y \right] \cdot \left[ 1 + \frac{m}{2} e^{j2\pi(f_{0x} x - v_0 t)} + c.c. \right] dx dy$$

$$= I_i \left( A_r(0,0) + \frac{m}{2} A_r(f_{0x}, 0) e^{j2\pi v_0 t} + c.c. \right).$$

Here $A_r(f_x, f_y)$ represents the complex Fourier transform of the intensity response of the object encompassed by the finite illumination area, $I_i$ and $I_d$ are the incident and detected intensities, $f_{0x}$ and $v_0$ are the spatial and temporal frequencies of the illumination, m is the modulation depth, and c.c. represents the complex conjugate. Thus, the spatially-integrated flux 109-*a* scattered, reflected, transmitted, generated, and/or fluoresced by the object 102-*a* that may be illuminated by a moving sinusoidal pattern may oscillate in time, wherein the amplitude and/or phase of the oscillation may correspond to the strength and/or offset of the matching Fourier component present in the intensity response of the object 102-*a*. The combined detector signal 112-*a* due to the linear sum of moving sinusoidal illumination components 108-*a* may then be represented as a linear sum of time-varying sinusoidal signals, where the temporal frequency of each sinusoidal signal may be related to the corresponding spatial frequency in the object's illumination response as $v_0 = v_x f_{0x}$, where $v_x$ is the velocity of motion of the sinusoidal illumination. Therefore, individual Fourier components of the object may be recovered by time-domain Fourier analysis of the frequency-multiplexed detector signal 112-*a*. In one embodiment, where each moving sinusoidal spatial modulation component 105 may be used to measure a unique Fourier component of the object, the product of the velocity and spatial frequency of said spatial modulation component may be chosen to be unique.

It should be apparent to those skilled in the art that a variety of implementations of said embodiments is possible within the spirit and scope of this invention. The radiation 103-*a*-*i* may be visible and/or invisible, particulate and/or wavelike, and may be temporally and/or spatially coherent, as in the case of laser radiation, and/or partially coherent, as in the case of radiation from a Light Emitting Diode (LED). The two-dimensional spatial modulator 100-*a* may be transmissive and/or reflective and may take the form of a programmable grid of elements, such as a Liquid-Crystal (LC) array or a Digital Micromirror Device (DMD), a continuous structured medium, and/or a deformable surface or membrane. In one embodiment, the two-dimensional spatial modulator 100-*a* may include a radial combination of one-dimensional spatial modulators. Merely by way of example, system 180 may show an embodiment where a body of water perturbed by ultrasonic waves emanating from multiple actuators arranged at the periphery may be used as a two-dimensional spatial modulator 100-*a*-*i*, which may produce multiple moving sinusoidal components 105-*i*-*a*, 105-*i*-*b*, . . . , and 105-*i*-*n*. In some embodiments, the two-dimensional spatial modulator 100-*a* may include multiple one-dimensional spatial modulators, which may include but are not limited to a one-dimensional acoustic optic Bragg cell, a surface acoustic wave device, and/or a programmable grating device, such as grating light valve device. As another example, subsystem 185 shows an embodiment where a two dimensional LC array or DMD array 100-*a-ii* is programmed to produce multiple moving sinusoidal components 105-*ii-a* and 105-*ii-b* as part of the two-dimensional spatial modulator 100-*i*. The two-dimensional spatial modulator 100-*a-ii* may spatially modulate radiation 103-*a-ii*. Lens 190-*a-ii*. may also collimate radiation 103-*a-ii*. Although the preceding discussion treated an object illuminated with an intensity pattern, other spatially-varying properties of the illumination, such as polarization and/or wavelength, may also be used to probe structure present in the object 102-*a*. Furthermore, although a substantial portion of radiation 109-*a* coherently scattered by the object may typically be collected onto the detector 101-*a* to spatially integrate any localized structure present in the response, such as speckle, when radiation 109-*a* from the object 102-*a* is isotropic only a small portion may need to be collected. For example, in the case of a strong fluorescent response, the detection optical system 110-*a* may not be needed and a bare spectrally-filtered detector element 101-*a* positioned in relative proximity to the object 102-*a* may be sufficient to perform high-fidelity Fourier-domain measurements using these techniques.

Figure 2:
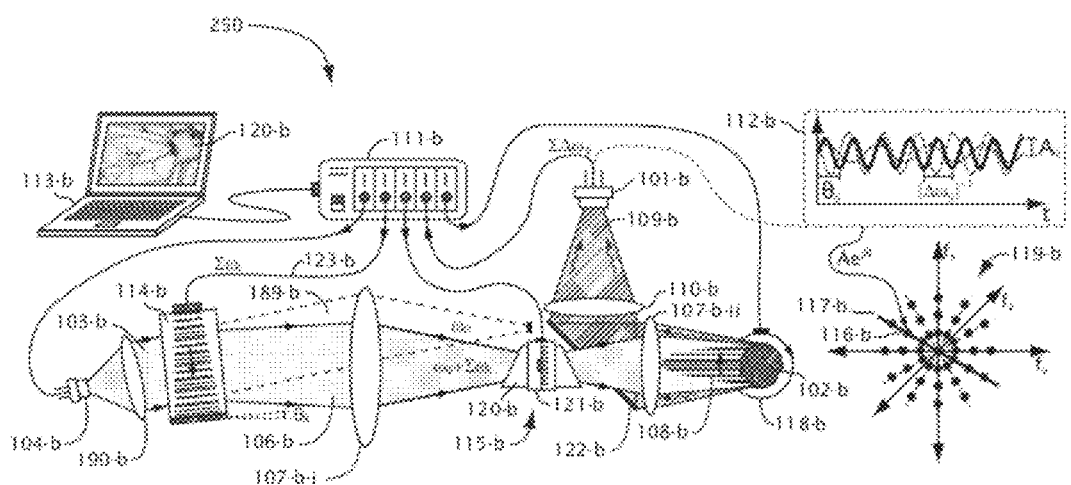
FIG. 2 illustrates a system where an image of an object may be reconstructed by illuminating the object with a radiation wavefront that has been spatially modulated with multiple moving sinusoidal patterns using an acousto-optic Bragg cell and rotated using a prism, detecting the scattered, reflected, transmitted, fluoresced, or otherwise generated response with a single-element detector, and computing the image from the measured Fourier components using a processor, in accordance with various embodiments.

FIG. 2 illustrates a Fourier domain sensing system 250, in accordance with various embodiments. The system 250 shows an object 102-*b* that may be illuminated with structured illumination 108-*b* generated using a one-dimensional spatial modulator 114-*b* and a wavefront rotating device 115-*b*. While it is possible to measure multiple Fourier components 116-*b* simultaneously along a single direction in this embodiment, other directions or radial "slices" 117-*b* in Fourier space may be accessed sequentially. Furthermore, the object 102-*b* itself may be rotated or tilted using a mechanical stage 118-*b* to measure different Fourier slices in the three-dimensional Fourier space 119-*b*, from which a two- or three-dimensional object characteristic or image 120-*b* can be reconstructed. Due to the availability of high-speed one-dimensional spatial modulators, Fourier measurements may be acquired very rapidly in some embodiments, especially when a non-mechanical wavefront rotating device 115-*b* may be used. Whereas parallel acquisition of multiple Fourier components 116-*b* along a Fourier slice 117-*b* may increase measurement speed, sequential acquisition of individual Fourier samples may make it possible to attain a very large Depth of Field, which is substantially limited only by the extent of axial invariance of the illumination pattern 108-*b*. During sequential measurements of individual Fourier components, the axial extent of the sinusoidal interference patterns illuminating the object may be very large, which may make it possible to attain a millimeter-scale Depth of Field while maintaining wavelength-scale resolution, merely by way of example.

In one embodiment, radiation 103-*b* emitted by a radiation source 104-*b* with optical frequency $\omega_0$ may be collimated using a lens 190-*b* and spatially modulated using a one dimensional spatial modulator 114-*b*. Merely by way of example, the one dimensional spatial modulator may be an acousto-optic Bragg cell. Whereas the $0^{th}$-order transmitted radiation 189-*b* may be blocked near a Fourier plane, the diffracted $1^{st}$ order radiation wavefront 106-*b* may be rotated using a prism 120-*b*, such as a Dove prism, and/or an arrangement of mirrors mounted on a rotation stage 121-*b*, and projected onto the object 102-*b*. In some embodiments, other diffraction orders may also be utilized. System 250 may includes one or more lenses, such as 107-*b-i* and 107-*b-ii*, which may be used to facilitate projecting wavefront 106-*b* onto the object 102-*b*. In some embodiments, other diffraction orders of the radiation may be utilized. Radiation 109-*b* scattered, reflected, transmitted, fluoresced, or otherwise generated by object 102-*b* in response to the structured illumination 108-*b* may be directed by means of a beam splitter 122-*b* and additional optics, such as lens 110-*b* onto a single-element detector 101-*b*. An electronic control system 111-*b* may be used to program the one dimensional spatial modulator 114-*b*, control a combination of wavefront and object rotation stages 115-*b*, 118-*b*, acquire the time-varying detector signal 112-*b*, and/or optionally amplitude-modulate the radiation source 104-*b* in order to convert the time-varying detector signal 112-*b* to a more accessible range of frequencies. A processor 113-*b* in communication with the control system 111-*b* may used to process the acquired detector signal 112-*b* to compute the Fourier components 116-*b* of the object 102-*b* and use this information to characterize the object and/or reconstruct its image 120-*b*, merely by way of example.

In one embodiment, the one dimensional spatial modulator 114-*b* such as a Bragg cell, for example, may be driven with a compound electronic signal 123-*b* comprising multiple sinusoidal waveforms. Each sinusoid waveform may be described by a combination of amplitude, phase, and/or temporal frequency, such that at any time the drive signal can be characterized by a combination of frequencies, $\Sigma\omega_i$. A piezoelectric transducer (part of Bragg cell 114-*b*) converts the electronic signal into an acoustic waveform, which perturbs the index of refraction of the Bragg cell crystal (part of Bragg cell 114-*b*) via the photoelastic effect, resulting in a one-dimensional volume phase hologram traveling through the Bragg cell crystal at the velocity of sound. To maximize diffraction efficiency, the radiation may enter the Bragg cell 114-*b* at an angle with respect to the acoustic velocity normal substantially close to the Bragg angle, $\theta_B$. Furthermore, the Bragg cell 114-*b* may be driven sufficiently weakly so that the diffraction efficiency varies substantially linearly with the electronic drive signal power. Due to the acousto-optic Doppler effect, radiation diffracted by each spatial frequency present in the traveling volume hologram may acquire a corresponding temporal frequency shift, such that the $1^{st}$ order diffracted radiation wavefront 106-*b* may be characterized by a combination of frequencies, $\omega_0+\Sigma\omega_i$. Furthermore, each spatial frequency present in the hologram may diffract light at a different angle, resulting in a compound interference pattern 108-*b* that can be considered as a combination of sinusoidal intensity patterns moving across the object 102-*b*, where the spatial frequency of each sinusoid may be linearly related to the corresponding temporal difference frequency $\Delta\omega_{ij}$, present in the electronic drive signal 123-*b*. In this way, patterns present in the moving volume hologram may be projected onto the object 102-*b*.

As in the case of the embodiment illustrated in FIG. 1 and described earlier, each moving sinusoidal intensity component present in the illumination 108-*b* may produce an oscillating signal contribution at the detector 101-*b*, such that the compound detector signal 112-*b* can be characterized by a combination of frequencies, $\Sigma\Delta\omega_{ij}$. The amplitude, $A_{ij}$, and phase, $\theta_{ij}$, of each oscillating signal component may correspond to the magnitude and phase of the corresponding spatial Fourier coefficient 116-*b* of the object 102-*b*. In this way, multiple Fourier components of the object 102-*b* can be measured simultaneously and recovered by time-domain Fourier analysis of the frequency-multiplexed detector signal. In one embodiment, where each acoustic beat pattern in the Bragg cell 114-*b* may be used to measure a unique Fourier component of the object, the difference frequencies $\Delta\omega_{ij}$, present in the Bragg cell 114-*b* drive signal may be chosen to be unique.

It should be apparent to those skilled in the art that a variety of implementations of the embodiment in FIG. 2 are possible within the spirit and scope of this invention. For example, the one-dimensional spatial modulator 114-b may be reflective, as in the case of a Surface Acoustic Wave (SAW) device or a programmable grating device, such as Grating Light Valve (GLV) device. Some embodiments may also utilize a two-dimensional modulator as discussed with respect to FIG. 1. The wavefront rotation device 115-b may also be reflecting, including a retro-reflecting prism and/or an arrangement of mirrors, or may be implemented without moving components so that the illumination can be rotated faster than the acoustic propagation time across the optical aperture. In the latter case, sequential measurements of Fourier components may be accomplished by rotating the illumination for each position of the illumination pattern before varying the spatial frequency, rather than the other way around. Measurements along different Fourier slices 117-b can be accomplished by rotating the illumination, rotating or tilting the object 102-b, or any combination of these techniques. To improve signal contrast, the beam splitter 122-b that may be used to separate radiation 109-b due to the object from the illumination 108-b may be polarizing when the object response is scattered, or dichroic when the response is fluoresced. Due to the nearly common path of the diffracted beams, the radiation may be temporally and spatially coherent, as in the case of laser radiation, or partially coherent, as in the case of radiation from a Light Emitting Diode (LED), merely by way of example.

Fourier Optics can be used to derive the dynamic Optical Transfer Function (OTF) of the illustrated system 250 and the other systems illustrated with in other figures. Consider the effect of an arbitrary RF drive signal 123-b, s(t), on the detected intensity 112-b, $I_d(t)$, under coherent illumination. When the Bragg cell 114-b is operated in the linear regime, the incident field 103-b is modulated along the y' axis by the propagating acoustic pattern in proportion to the time-delayed RF signal 123-b, convolved in time with the acousto-optic impulse response, $h_a(t)$, and windowed by the optical and acoustic beam overlap cross-section, a(x',y'), which is reflected in the following equation:

$$U_a(x', y', t) = a(x', y')\left[h_a(t) * s(t) * \delta\left(t - \frac{t_a}{2} + \frac{y'}{v_s}\right)\right]e^{j\omega t} + c.c.$$

where $v_s$ is the speed of sound in the crystal, and $\omega$ is the optical frequency. Before illuminating the object, the diffracted field 106-b is convolved with the one-dimensional impulse response of the projection system, p(y), and demagnified by a factor M. The resulting interference pattern 108-b is then multiplied by the object's intensity response 102-b, $|\sigma(x,y)|^2$, and spatially integrated at the detector 101-b. The detected signal may be represented as the following equation:

$$I_d(t) = \int\int_{-\infty}^{\infty} |\sigma(x,y)|^2 \left|p(y) * \left[a(Mx, My)s_a\left(t - \frac{t_a}{2} + \frac{My}{v_s}\right)\right]\right|^2 dy\,dx$$

where $F_y\{\ \}$ represents a one-dimensional slice through the spatial Fourier transform. Converting from temporal to spatial frequency using $v=f_y v_s/M$ in post-processing, moving the $F_y\{\ \}$ term outside the integral, and recognizing the integral as another Fourier slice, one may obtain the one-dimensional optical transfer function, represented in the following equations:

$$OTF^{1D}(f_y) = \frac{F_y\{|\sigma_r(x, y)|^2\}}{F_y\{|\sigma(x, y)|^2\}} = e^{j\pi f_y v_s t_a/M} \cdot \{\mathcal{H}(f_y) \star \mathcal{H}(f_y)\}$$

$$\mathcal{H}(f_y) = \mathcal{P}(f_y) \cdot \left[\mathcal{A}\left(\frac{f_y}{M}\right) * S_a\left(\frac{v_s f_y}{M}\right)\right].$$

Here $F_y\{|\sigma_r(x,y)|^2\}$ is a Fourier slice of the reconstructed object, * stands for correlation, and $\mathcal{P}(f_y)$, $S_a(f_y)$, and $\mathcal{A}(f_y)$ are one-dimensional Fourier transforms of p(y), $s_a(y)$, and the projection of a(x,y), respectively. One can see from this result that electronic control of the RF signal allows adjustment of the $OTF^{1D}$ of the system on a slice-by-slice basis. By applying the Fourier Slice Theorem, one can thereby synthesize a dynamic two- or three-dimensional OTF and obtain a reconstruction of the object using the following equations:

$$OTF^{2D}(f_x, f_y) = W(f_x, f_y) \int_0^\pi OTF_\theta^{1D}(f_x \sin\theta + f_y \cos\theta) d\theta$$

$$|\sigma_r(x,y)|^2 = F^{-1}_{f_x, f_y}\{OTF^{2D}(f_x, f_y) F_{x,y}\{|\sigma(x,y)|^2\}\}.$$

where $\theta$ is the Fourier slice angle and $W(f_x, f_y)$ is an angle-independent weighting filter accounting for sparser sampling of Fourier space at higher frequencies. In conjunction with a feedback system, it may thus be possible, for example, to dynamically correct coarse phase errors in the pupil function (e.g. due to flexing of a large reflector), and/or to adapt the OTF to a changing scene. The dynamic OTF also may enable Fourier-domain filtering in real time and without the loss of light associated with amplitude-mask-based filtering. This capability may not be only helpful for optical processing applications, but may also be used to optimize imaging sensitivity or measurement time based on a priori information about the Fourier content of a class of objects, such as thin cellular membranes or grid-based semiconductor structures, enabling a form of compressive imaging.

Figure 3A:
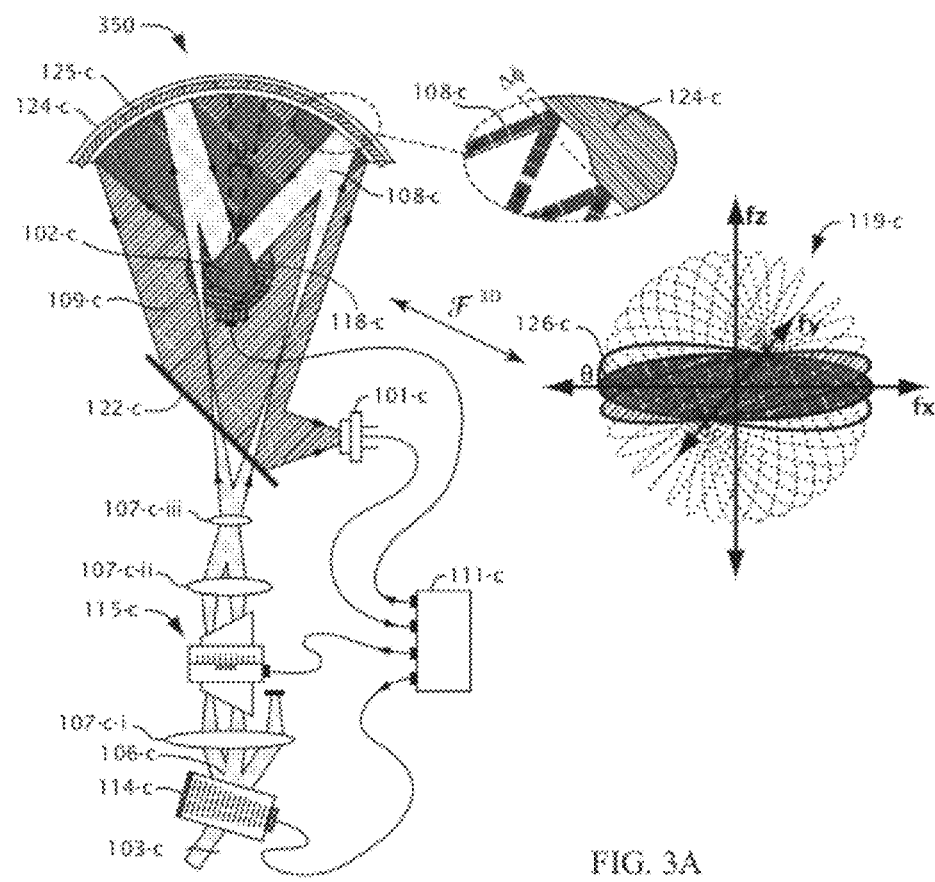
FIG. 3A illustrates a system that may be used for measuring tilted planes in Fourier space and probing three-dimensional structures by tilting the object and/or tilting the illumination and using an electronically phase-compensated large low-precision reflector to project structured illumination and collect the object's scattered, reflected, transmitted, fluoresced, or otherwise generated response onto a single-element detector, in accordance with various embodiments.

FIG. 3A illustrates an embodiment of another Fourier domain sensing system 350, in accordance with various embodiments. System 350 includes a reflector 124-c, which may be a large, low-precision reflector. Reflector 124-c may be used to project the illumination 108-c and collect the scattered, reflected, transmitted, fluoresced, or otherwise generated radiation 109-c from the object 102-c onto a single-element detector 101-c via a dichroic or polarizing beam splitter 122-b. Such a large aberration-compensated reflector can be many centimeters in diameter and can be positioned many centimeters or even meters away from the object, while maintaining wavelength-scale resolution and millimeter-scale depth of field. The reflector surface 124-c may need to be optically-precise only within a small fraction of its Numerical Aperture (NA), where this fraction is approximately the inverse of the number of resolvable spots, or equivalently, the time-bandwidth product of the Bragg cell 114-b, which can exceed several thousand. Coarser phase errors, $\Delta\phi$, in the reflecting surface, however, may be corrected by electronically adjusting the phase of the acoustic waveform or in post-processing. A calibration step may be performed to measure the phase errors by temporarily replacing the object with a known target such as a small fluorescent bead, a combination of gratings, or a Fresnel zone plate. Alternatively, known constraints about the object itself may be used to extract the phase errors in the reflector surface. The reflector may be machined out of metal, electroformed, or even assembled from a mosaic of flat mirrors 125-c. In one embodiment, the reflector surface may be ellipsoidal, with one of the foci located at the object, and the other at a spatial modulation conjugate plane. In one embodiment, the reflector 124-c may include multiple mirror segments that can be folded for storage.

Also illustrated is an embodiment wherein it is possible to measure individual Fourier components in three dimensions, from which a three-dimensional image can be reconstructed. As described earlier, by rotating the illumination pattern or the object itself about the illumination axis or by using a two-dimensional spatial modulator, it is possible to measure Fourier components of the object lying on a plane 126-c in the three-dimensional Fourier space 119-c. Additional tilted Fourier planes can be measured by tilting the object using a mechanical stage 118-c and/or by tilting the illumination axis, which can be accomplished, for example, through rapid electronic control of the center frequency of the signal driving the one dimensional spatial modulator such as Bragg cell 114-c. While the range of illumination axis tilts may be limited by the NA of the projection system, as illustrated in Fourier space using heavy lines of Fourier space 119-c, by tilting the object it is possible to fully sample the three-dimensional Fourier space, as illustrated by tilted Fourier planes with dotted lines of Fourier space 119-c. It should be apparent to those skilled in the art that it is not necessary to measure one plane at a time in Fourier space. The operations of rotating and tilting the object with respect to the illumination pattern may be performed in any sequence to build up the desired three-dimensional distribution of Fourier samples.

Figure 3B:
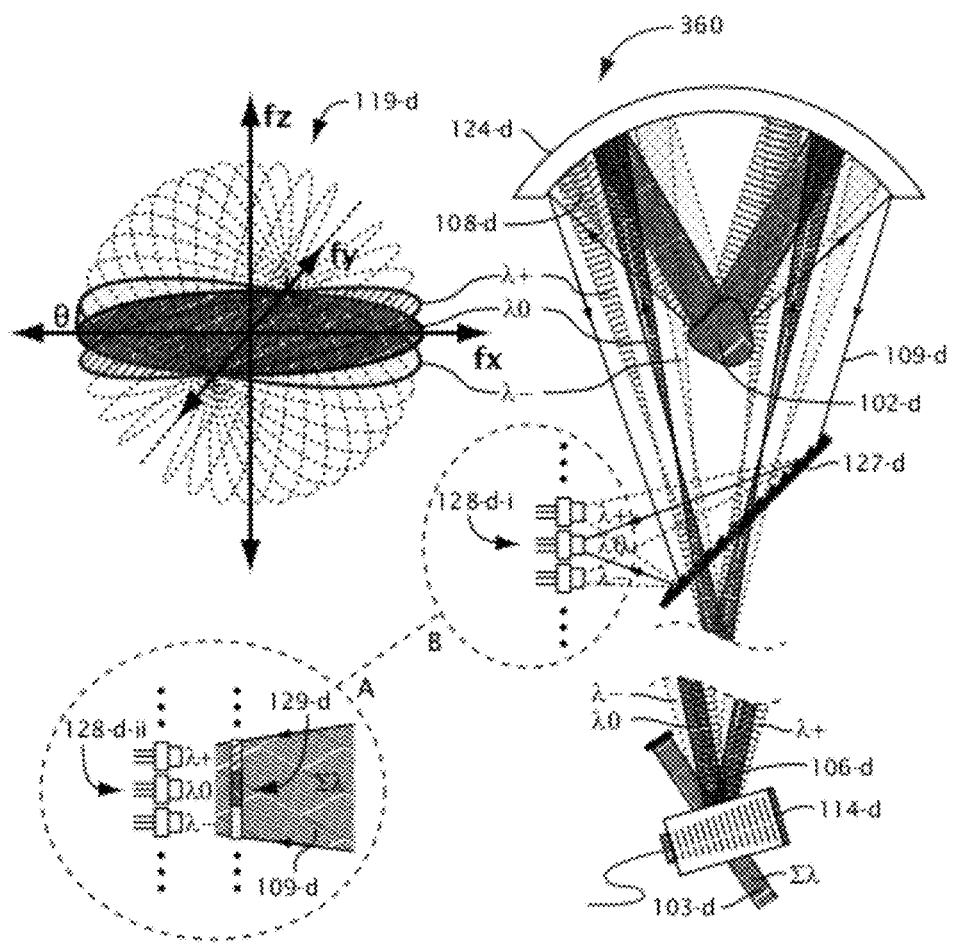
FIG. 3B illustrates a system that may be used for measuring tilted planes and/or slices in Fourier space and probing three-dimensional structures by using spectrally distributed illumination, dispersive elements and/or filters, and multiple detectors to measure multiple groups of Fourier components in parallel using different wavelengths.

FIG. 3B illustrates another embodiment of a Fourier domain sensing system 360 where three-dimensional Fourier slices or planes having different tilts may be measured simultaneously using a source of broadband radiation 103-d, rather than by sequentially tilting the object or the illumination axis. This parallel spectrally-multiplexed technique may greatly speed up the acquisition of three-dimensional images. In this embodiment, the spatial modulator 114-d may impart different diffraction angles onto different spectral components of the modulated radiation 106-d, three of which are labeled in increasing order of wavelength as $\lambda-$, $\lambda 0$, and $\lambda+$. As a result, the axis of illumination 108-d due to each spectral component may be unique, thereby mapping different tilts of Fourier slices or planes to different illumination wavelengths. When the signal from the object 109-d is due to scattered light, signals from spectrally-coded loci in Fourier space can be separated using a dispersive element 127-d, such as a grating, onto an array of detectors 128-d-i. Alternatively, a bank of spectral filters 129-d placed in front of a detector array 128-d-ii can be used instead of a dispersive element. When the detected signal is due to fluorescence, the object can be labeled with a combination of fluorophores with substantially non-overlapping absorption spectra to separate signals due to different components of the illumination spectrum.

It should be apparent to those skilled in the art that a variety of implementations of the embodiment in FIGS. 3A and 3B are possible within the spirit and scope of this invention, including such variations as are seen with embodiments of FIG. 1 and FIG. 2. Furthermore, various components of FIGS. 3A and 3B may be labeled with first reference numbers that may be described above along with FIGS. 1 and/or 2. A second label on a component may merely reflect that the component is part of a specific figure.

Figure 4:
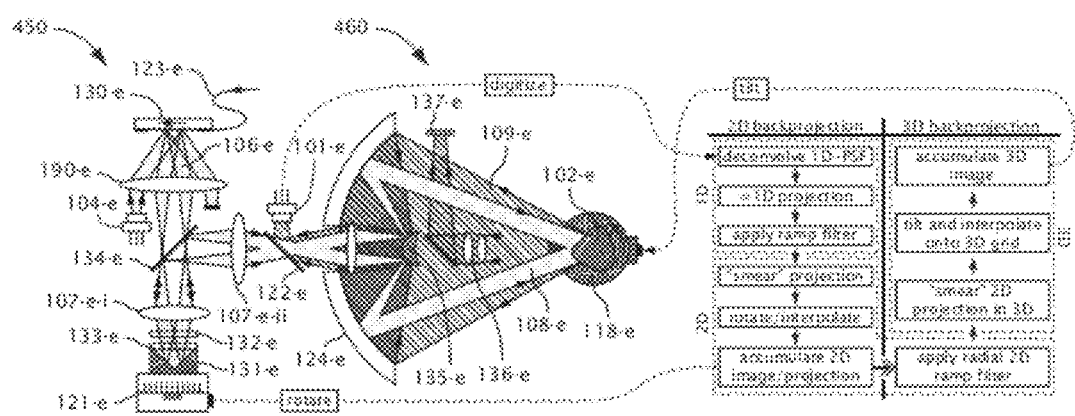
FIG. 4 illustrates a system wherein illumination spatially modulated using a reflecting Surface Acoustic Wave device and rotated using a retro-reflecting prism or mirror arrangement may be projected onto the object using an in-line reflector system, the object's response is detected with a single-element detector, and a two- or three-dimensional image is reconstructed using the tomographic filtered backprojection algorithm in real time or in post-processing, in accordance with various embodiments.

FIG. 4 illustrates another Fourier domain sensing system 450, in accordance with various embodiments. In system 450, illumination patterns may be generated using a reflective Surface Acoustic Wave (SAW) device 130-e, rotated using a retro-reflecting right-angle prism or mirror arrangement 131-e, and projected onto the object using a large low-precision reflector 124-e. The SAW device 130-e, which may be fabricated by patterning an inter-digitated transducer and depositing a reflective surface on a Lithium Niobate wafer in some embodiments, is functionally similar to the acousto-optic Bragg cell described earlier. However the propagating acoustic waves of the SAW device may perturb the shape of a reflecting surface rather than the index of refraction in a bulk crystal as with an acousto-optic Bragg cell. Because SAW perturbations are typically only a small fraction of the optical wavelength, diffraction efficiency may be much lower than in the case of the volume-holographic Bragg cell. A SAW device 130-e can be inexpensive to manufacture, does not require Bragg-matching, and can work in wavelength regimes where acousto-optic crystals are not available, including UV and X-rays. The retro-reflecting illumination rotator 131-e may be easier to align than a transmissive one such as a Dove prism, may introduce fewer aberrations, and when implemented using mirrors may work in wavelength regimes where prisms may not be available. As with a transmissive prism, the illumination pattern is rotated by the retro-reflector 131-e at twice the rate of the rotation stage 121-e. Since a Fourier plane can be fully sampled with 180 degrees of rotation, the stage revolution rate may be quadrupled when calculating the image acquisition rate. A pair of retarders, one 132-e stationary and the other 133-e that may be mounted on the rotation stage, can be used to preserve the linear polarization state as the pattern is rotated, which may maximize the coupling efficiency of the polarizing beam splitter 134-e. In this embodiment, the fixed quarter-wave retarder 132-e is used to turn the incoming linear polarization into circular, while the other rotating retarder 133-e, its fast axis aligned with the edge of the right-angle prism or mirrors, is used to nullify the polarization effects of the retro-reflector so that polarization behavior of the rotating elements taken together is that of a mirror and the system functions as an optical isolator.

The diffracted and rotated $1^{st}$-order radiation 106-e from the SAW device 130-e may be coupled into the projection system 460 via a small central aperture in the large reflector 124-e and may be directed back onto the reflector 124-e via a secondary mirror 135-e, which magnifies the diffraction angle. In some embodiments, other diffracted orders of the radiation 106-e may also be utilized. As in FIGS. 3A and 3B, radiation from the object 109-e in response to the illumination 108-e may be collected using the same reflector 124-e and directed onto a single-element detector 101-e via a dichroic or polarizing beam splitter 122-e. In one embodiment, the reflector 124-e may be ellipsoidal in shape, with one of its foci located at the object 102-e and the other coinciding with the focus of the paraboloidal secondary mirror 135-e. In some embodiments, a miniature optical system 136-e may be placed just behind the secondary mirror 135-e to form a low-resolution image onto an imaging detector array 137-e such as a CCD. This low resolution image can then be combined with the reconstructed high resolution image to fill in the low spatial frequencies that would otherwise be lost due to shadowing by the secondary mirror, while still maintaining a large depth of field. Furthermore, the imaging detector 137-e and optical system 136-e may be the primary imaging instrument, whereas the Fourier domain sensing system 450 may be used as a means to enhance the resolution of the optical system 136-e. Moreover, in addition to direct acquisition of low-resolution images, the imaging detector 137-e can also be used instead of or in addition to the single-element detector 101-e to capture and to spatially integrate a portion of the object radiation 109-e emitted or scattered in response to the structured illumination 108-e. This can be accomplished by summing the signals from multiple detector elements comprising the imaging detector array in some embodiments.

Also illustrated is a method for reconstructing an image of the object from the time-domain detector signal that may be utilized with embodiments such as system 450. As described above, the one-dimensional Optical Transfer Function ($OTF^{1D}$), and therefore the one-dimensional point spread function ($PSF^{1D}$), of the system may be determined by the RF signal 123-*e* driving the acousto-optic spatial modulator 130-*e*. For each measured Fourier slice, by deconvolving the digitized detector signal with the $PSF^{1D}$, a one-dimensional projection of the object may be obtained along the lateral direction normal to the Fourier slice. A two-dimensional image can be reconstructed by applying the Filtered Back-projection (FBP) algorithm, a method commonly used in the field of projection tomography to reconstruct a two-dimensional image from multiple one-dimensional projections. The image may be obtained using this algorithm by filtering each one-dimensional projection using a ramp filter to compensate for sparse Fourier sampling at high spatial frequencies, smearing the filtered projection in two dimensions along the projection direction, and coherently accumulating the smeared projections. Unlike rectilinear direct Fourier transform techniques, this process can be performed entirely in real space potentially resulting in fewer interpolation artifacts, and makes it possible to synthesize the image in real time, slice-by-slice, rather than in post-processing. Furthermore, because the Fourier Slice Theorem applies in three as well as two dimensions, the FBP algorithm may be extended straightforwardly to reconstruct a three-dimensional image from measurements mapping to multiple tilted planes in Fourier space, such as those shown in FIG. 3. Because this tomographic approach to three-dimensional imaging can be sensitive to radiation emitted from locations within the entire illumination volume, it can be more light-efficient than confocal optical sectioning techniques in which out-of-focus light is rejected.

It should be apparent to those skilled in the art that a variety of implementations of the embodiment in FIG. 4 are possible within the spirit and scope of this invention, including such variations as are seen with embodiments of FIGS. 1, 2, 3A, and 3B. Furthermore, various components of FIG. 4 may be labeled with first reference numbers that may be described above along with FIGS. 1, 2, 3A, and/or 3B. A second reference label on a component may merely reflect that the component is part of a specific figure.

Figure 5:
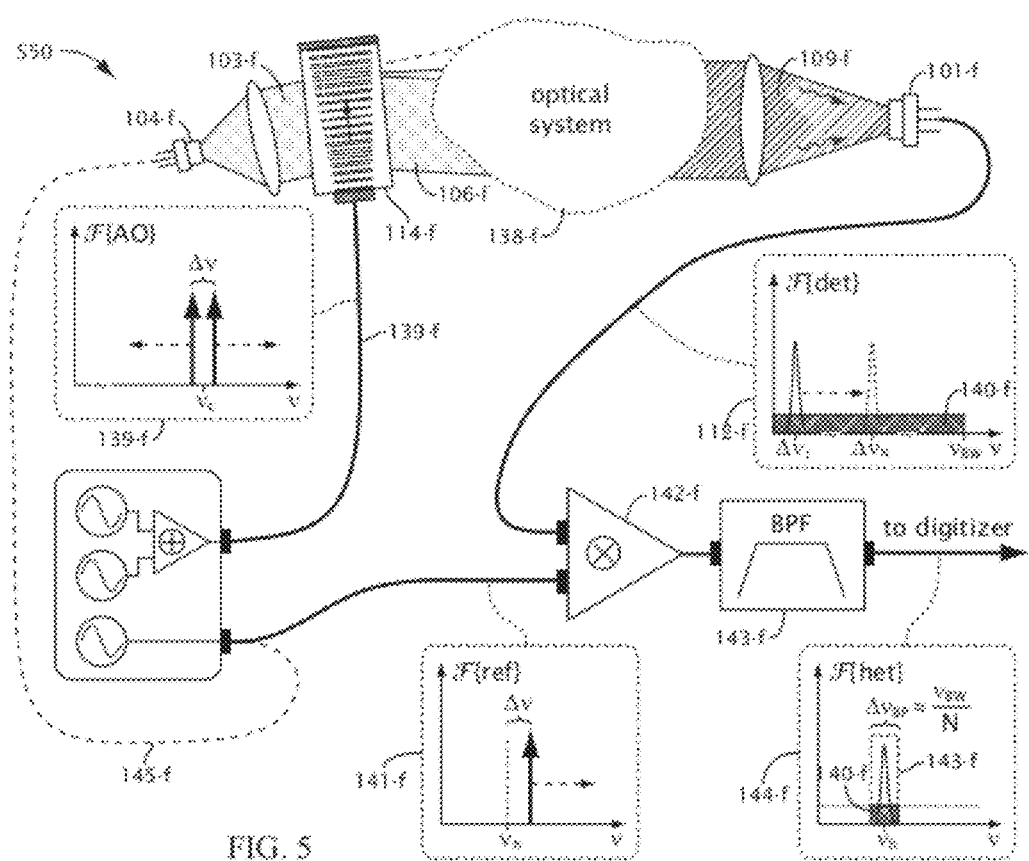
FIG. 5 illustrates a system that may utilize heterodyne detection to reduce the noise bandwidth of the measurement and the required digitization rate, in accordance with various embodiments.

FIG. 5 illustrates a Fourier domain sensing system 550, in accordance with various embodiments, that employs heterodyne detection and signal processing. The optical system 138-*f* for illumination projection and signal collection may involve any of the systems disclosed as in FIGS. 1, 2, 3A, 3B, 4, 6, 7, and 8. In one embodiment, the acousto-optic spatial modulator 114-*f* may be driven with a double-sided chirp signal 139-*f* having linearly time-varying difference frequency, $\Delta v$, and centered at the Bragg frequency, $v_c$, resulting in rapid sequential measurement of spatial frequencies along a Fourier slice. The detected signal 112-*f* produced as a result of chirped sequential Fourier sampling may itself be chirped in frequency, varying in time with the difference frequency $\Delta v$. If the detector signal is processed directly, photon shot noise as well as other white noise processes 140-*f* from the entire detector bandwidth, $v_{BW}$, may corrupt the digitized signal. On the other hand, by electronically mixing and/or multiplying the detector signal 112*d*, for example, with a synchronously chirped reference signal 141-*f* using an analog circuit 142-*f*, the chirped detector signal may be modulated onto a fixed carrier at the heterodyne offset frequency, $v_h$. By passing the heterodyne signal through a bandpass filter 143-*f* with a bandwidth of $\Delta v_{BP}$ centered at $v_h$, it may be possible to reduce the noise bandwidth 140-*f* of the signal to be digitized 144-*f* by a factor of N, where N is the number of resolvable spatial frequencies in the Fourier slice and may be determined by the time-bandwidth product of the acousto-optic Bragg cell 114-*f*. Furthermore, by choosing $v_h$ to be low, the digitizer sampling rate may be reduced by up to a factor of N, making it possible to use a lower bandwidth, higher dynamic range digitizer. In some embodiments, the same heterodyne detection effect can be achieved optically instead of electronically by modulating the amplitude of the illumination source 104-*f* using the chirped reference signal, as illustrated by the dashed line 145-*f*. In this case, the detector signal 112-*f* may be passed directly through the bandpass filter 143-*f* without mixing. Such optical heterodyne detection may reduce the detector bandwidth requirement by up to a factor of N and may avoid nonlinearities associated with electronic mixing and multiplication.

It should be apparent to those skilled in the art that a variety of implementations of the embodiment in FIG. 5 are possible within the spirit and scope of this invention, including such variations as are seen with embodiments of FIG. 1-4. Furthermore, various components of FIG. 5 may be labeled with first reference numbers that may be described above along with FIGS. 1, 2, 3A, 3B, and/or 4. A second reference label on a component may merely reflect that the component is part of a specific figure.

Figure 6:
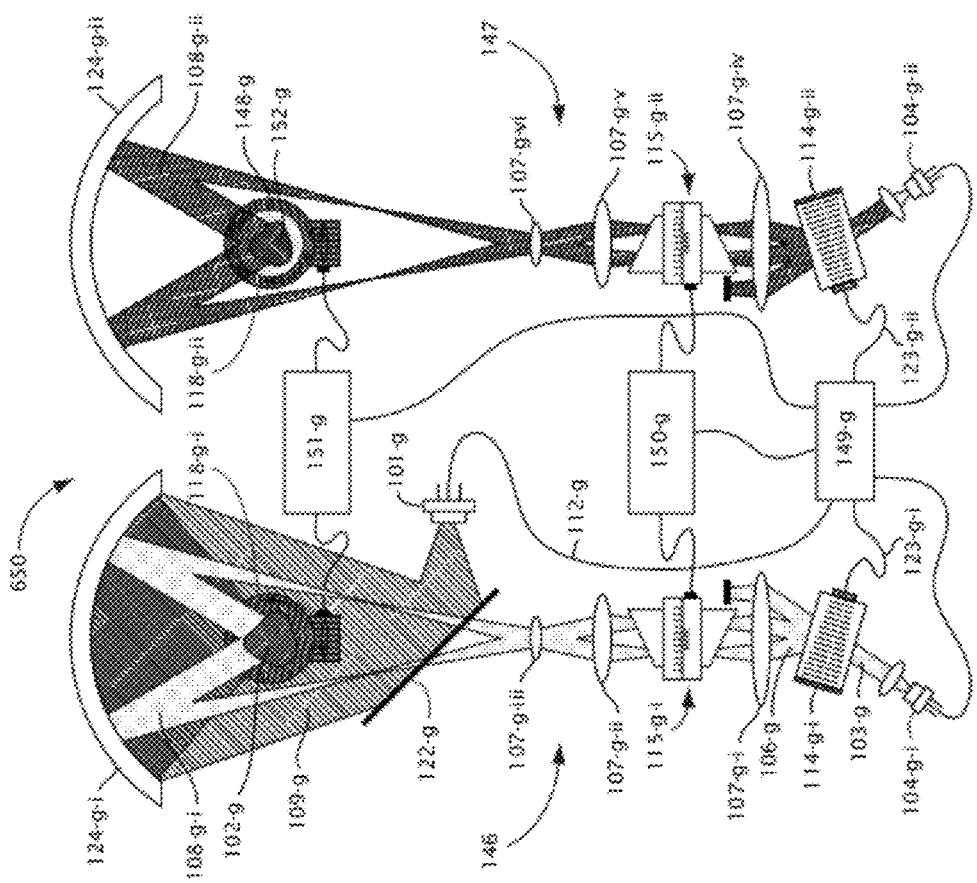
FIG. 6 illustrates a system wherein a Fourier analysis system may be interfaced with a nearly identical Fourier synthesis system for synchronously writing Fourier components of the object into a suitable bias-subtracting recording medium, in accordance with various embodiments.

FIG. 6 illustrates a Fourier domain sensing and writing system 650, in accordance with various embodiments that involves a three-dimensional holographic copier. In some embodiments, the Fourier domain sensing and writing system 650 may include a Fourier domain sensing system 146 such as those illustrated in FIGS. 3A and 3B (systems 350 and 360) for example. Other Fourier domain sensing systems may also be used in some embodiments of system 650. System 146 may be controlled synchronously with an Fourier domain writing system 147. In one embodiment, the writing system 147 may be similar to the sensing system 146, except that no radiation from the object 109-*g* is detected by system 147. Rather, a suitable recording medium 148-*g* may be used in place of the object. A controller 149-*g* may be used to produce the drive signals for the light sources 104-*g-i*, 104-*g-ii* and spatial modulators 114-*g-i*, 114-*g-ii* in the sensing and writing systems 146 and 147 respectively, to process the detector signal 112-*g* from the sensing system to compute Fourier components of the object 102-*g* and to synchronously control the drivers 150-*g* and 151-*g* for the rotation 115-*g-i* and 115-*g-ii* and tilt 118-*g-i* and 118-*g-ii* stages of the sensing and writing systems. In this embodiment, one or more Fourier components along a slice in Fourier space may be first measured by the sensing system 146 as described above, either simultaneously using frequency-multiplexed illumination or sequentially using a frequency-stepped drive signal 123-*g-i*. Additionally, the sensing system radiation source 104-*g-i* may be modulated in amplitude to step the phase of the structured illumination or to implement heterodyne sensing as described earlier. After the amplitudes and phases of the measured Fourier components along a Fourier slice are computed, the spatial modulator 114-*g-ii* in the writing system 147 may be programmed with a waveform 123-*g-ii* synthesized from the up-shifted coherent sum of these measured Fourier components. Once the synthesized pattern fills the spatial modulator 114-*g-ii*, the writing system light source 104-*g-ii* may be briefly pulsed, thereby illuminating 108-*g-ii* the recording medium 148-*g* with a stationary pattern comprising the measured Fourier components. This process may be repeated as additional Fourier components along the Fourier slice are measured and as the object 102-*g* and recording medium 148-g are synchronously rotated and/or tilted to copy additional Fourier slices and build up an image 152-g of the object 102-g. Because Fourier components from separate measurements may be combined incoherently in the recording medium, a uniform bias may accumulate as a result of such optical Fourier synthesis. To avoid image saturation, a suitable recording medium that is sensitive to spatial intensity variations, but not uniform bias, such as a photorefractive medium, may be used. For two-dimensional recording, a bias-subtracting CCD detector can instead be used as a recording medium 148-g in which a fixed amount of accumulated charge may be removed from each well several times during the integration period as multiple patterns sequentially illuminate the CCD surface. Alternatively, with precise illumination control, a thresholding recording medium 148-g, such as photoresist, can be used to produce high-contrast recordings of weak accumulated patterns on top of a large uniform bias.

It should be apparent to those skilled in the art that a variety of implementations of the embodiment illustrated in FIG. 6 are possible within the spirit and scope of this invention. The reading and writing processes and the control of rotation and tilt stages may be synchronous or sequential. The projected patterns may be electronically or optically scaled or otherwise altered to synthesize a scaled, filtered, or otherwise modified replica 152-g of the object 102-g. The writing system 147 may be implemented within the same optical system as the reading system 146, so that the object 102-g may be replaced with the recording medium 148-g after the measurement process has completed to initiate the writing process. Alternatively, the object 102-g and recording medium 148-g may be placed side-by-side within the illumination field of the same system. Furthermore, the writing system 147 may be used independently from the sensing system 146 as an Fourier synthesis engine. The optical architectures of the sensing and writing systems may differ from the one shown and may resemble embodiments illustrated in the other figures, such as FIGS. 1, 2, 4, 3B, 5, 7, and 8. The spatial modulators 114-g may be one-dimensional as shown or two-dimensional. When a two-dimensional spatial modulator 114-g-ii is used in the writing system 147, two-dimensional coherently-synthesized patterns may be written into the recording medium 148-g, which may thereby reduce bias accumulation. Pulsing of the illumination, whether by strobing the light source and/or shuttering the illumination itself, may be used when the spatial modulation pattern is moving as in the case of an acousto-optic device. On the other hand, with parallel-programmable spatial modulators such as LCD or DMD arrays, illumination pulsing may not be necessary.

It should be apparent to those skilled in the art that a variety of implementations of the embodiment in FIG. 6 are possible within the spirit and scope of this invention, including such variations as are seen with embodiments of FIGS. 1-5. Furthermore, various components of FIG. 6 may be labeled with first reference numbers that may be described above along with FIGS. 1, 2, 3A, 3B, 4, and/or 5. A second reference label on a component may merely reflect that the component is part of a specific figure.

Figure 7:
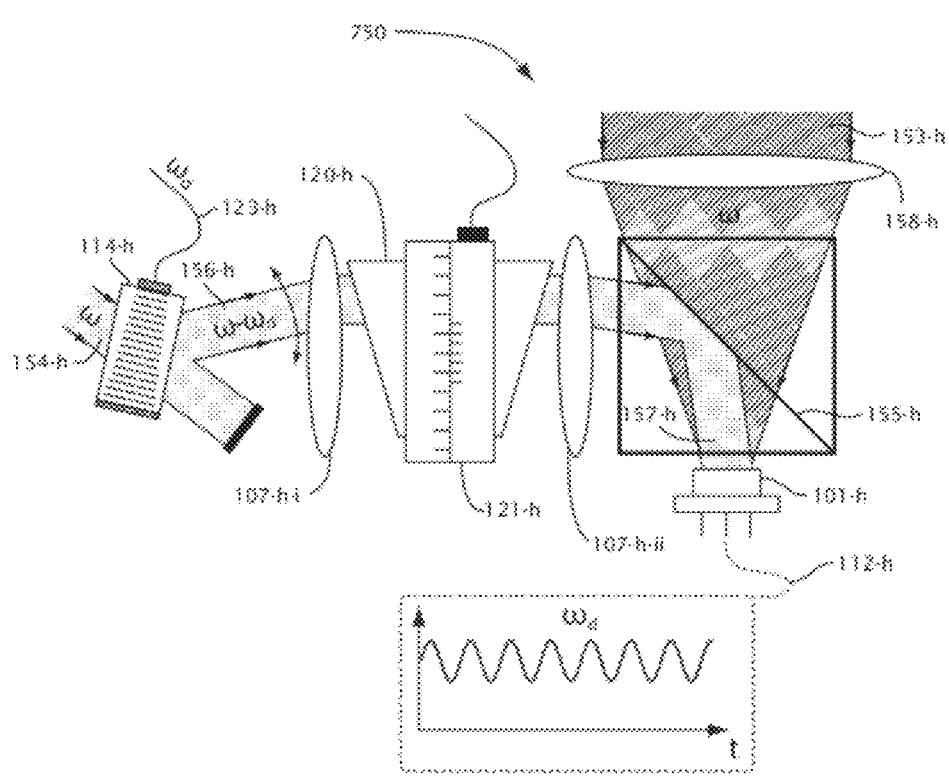
FIG. 7 illustrates a system for passive remote sensing that may measure the complex Fourier components of a coherent wavefront using an acousto-optically frequency-shifted and tilted reference beam, a rotating prism, and a single-element detector, in accordance with various embodiments.

FIG. 7 illustrates a passive remote coherent optical Fourier domain sensing system 750, in accordance with various embodiments. Whereas embodiments illustrated in FIG. 1-FIG. 6 may rely on illuminating the object with patterned radiation, in this embodiment plane wave components of a coherent wavefront 153-h of frequency ω from a remote object (not shown) may be measured passively. In one embodiment, a coherent reference beam 154-h with frequency ω may be diffracted by an acousto-optic spatial modulator 114-h driven with an RF tone 123-h of frequency $\omega_d$, rotated using a prism 120-h, and coherently combined using a beam splitter 155-h with the wavefront 153-h from the object on the surface of a single-element detector 101-h. The frequency of the diffracted beam 156-h may be Doppler-shifted by $\omega_d$ as a result. In this case, plane wave component of the object wavefront matching the direction of the Doppler-shifted and tilted reference beam 157-h illuminating the detector 101-h results in a beat signal at the detector output 112-h with frequency $\omega_d$, whereas other plane wave components produce interference patterns that are spatially integrated at the detector surface, generating little or no net signal modulation. By varying the tilt of the reference beam 154-h acousto-optically and changing its direction using the rotation stage 121-h, plane wave components of the wavefront 153-h from the object can be sequentially measured and processed in any of the numerous ways described in the context of the various structured illumination embodiments. Furthermore, by driving the Bragg cell 114-h with a compound signal 123-h with multiple frequencies, it may be possible to measure multiple plane wave components of the object wavefront 153-h simultaneously, in a manner as was described in the context of FIG. 1 and FIG. 2, for example. While in structured illumination embodiments such frequency-multiplexed measurements may reduce the depth of field due to tilt ambiguity, in this embodiment no analogous ambiguity or drawback may exist. The object wavefront 153-h may be collected onto the detector 101-h using an optical system such as a lens 158-h such that the phase gradient imparted on the wavefront 153-h by the optical system may be subtracted during processing of the detector signal to reveal the phase distribution of the incident wavefront.

This Fourier-domain wavefront analysis technique has several features that may be compared with other wavefront analysis methods. Because an individual single-element detector 101-h may be used to fully characterize the complex wavefront, this technique can be used in wavelength regimes where detector arrays are expensive or not available. The use of reflective spatial modulator and wavefront rotation technologies and a membrane beam splitter may extend this technique to EUV and X-ray regimes. In holography applications, the single-element detector 101-h can replace high-resolution film and/or high density imaging detectors in measuring the field and amplitude distribution of a coherent wavefront. Since the directions of the reference beam and the measured plane wave component are always co-aligned, this technique can be used to measure the entire complex Fourier transform of the wavefront with uniform accuracy. Furthermore, heterodyne detection and signal processing techniques can be applied to reduce the noise bandwidth as well as detector and digitization bandwidth requirements as described in the context of FIG. 5.

It should be apparent to those skilled in the art that a variety of implementations of the embodiment illustrated in FIG. 7 are possible within the spirit and scope of this invention. The coherent reference beam 154-h may be derived from the radiation used to illuminate the object, created by diverting a portion of the object wavefront 153-h, or produced by a frequency-locked laser. In the latter case, state-of-the art locking stability may not be necessary since the acousto-optic Doppler shift is typically in the range of tens to hundreds of megahertz. The wavefront rotation device 121-h may be reflecting, including a retro-reflecting prism and/or an arrangement of mirrors. Measurements along different directions can be accomplished by rotating the reference beam 157-h and/or rotating the object wavefront 153-h. As in embodiments described earlier, the spatial modulator 114-h may be a one dimensional device such as an acousto-optic Bragg cell, a SAW device, or a programmable grating device, or a two-dimensional device such as a multi-dimensional acousto-optic Bragg cell, LC device, or DMD array. In some embodiments with a two-dimensional spatial modulator 114-h wavefront rotation may not be necessary. The two dimensional Bragg cell can be a single device, or can comprise two orthogonal one-dimensional Bragg cells. Furthermore, with a two-dimensional Bragg cell, each reference beam tilt and orientation can be encoded with a unique RF frequency, making possible parallel frequency-multiplexed measurement of the two-dimensional complex Fourier transform of the object wavefront 153-h by frequency analysis of the time-domain detector signal.

It should also be apparent to those skilled in the art that a variety of implementations of the embodiment in FIG. 7 are possible within the spirit and scope of this invention, including such variations as are seen with embodiments of FIGS. 1-6. Furthermore, various components of FIG. 7 may be labeled with first reference numbers that may be described above along with FIGS. 1, 2, 3A, 3B, 4, 5, and/or 6. A second reference label on a component may merely reflect that the component is part of a specific figure.

Figure 8:
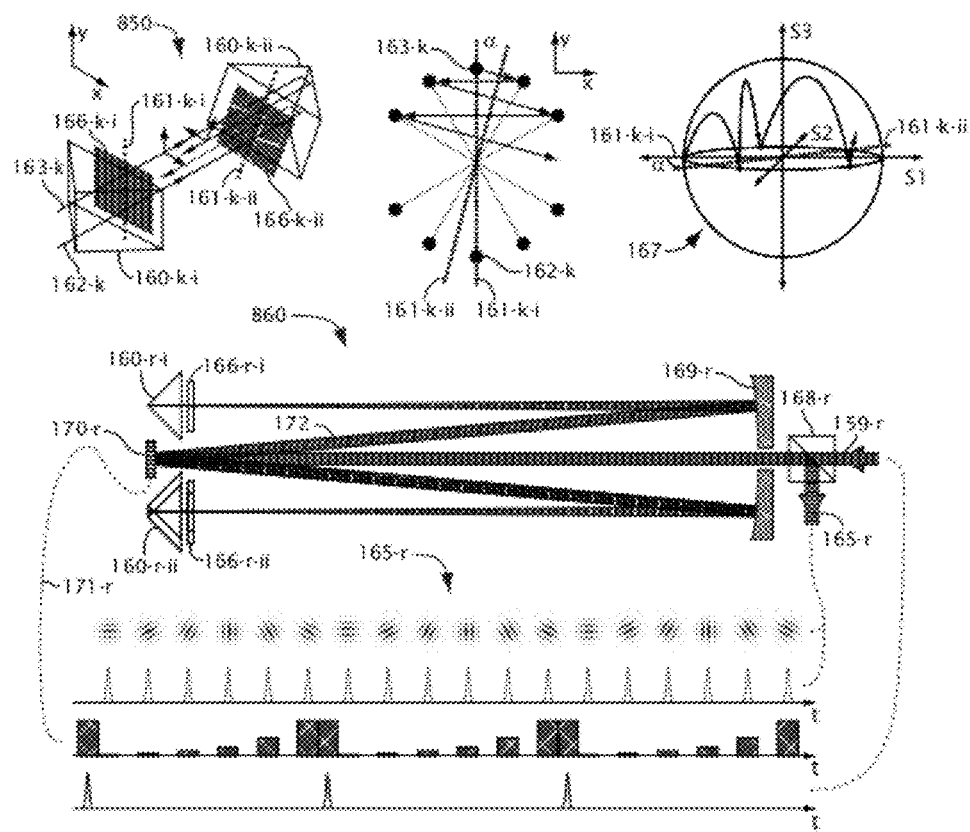
FIG. 8 illustrates a system that may provide a means for rotating a wavefront without moving components using mutually-tilted retro-reflecting prisms or mirrors inside a pulsed laser mirror cavity, in accordance with various embodiments.

FIG. 8 illustrates aspects of a Fourier domain sensing system 850 for rotating a wavefront without moving components employing retro-reflection, in accordance with various embodiments. Non-mechanical wavefront rotation may be accomplished by multiple reflection of a spatially modulated pulsed radiation wavefront by a pair of opposing right-angle retro-reflecting prisms or mirrors 160-k-i and 160-k-ii, collectively referred to as a "retro-reflector cavity", whose reflection symmetry axes 161-k-i and 161-k-ii are slightly tilted with respect to each other by an angle α. This process is illustrated for a pair of co-aligned radiation beams 162-k and 163-k. With each pass through the retro-reflector cavity, the transverse pattern defined by the two beams is incrementally rotated by an angle 2a and a fraction of the radiation may be coupled out of the cavity, producing a sequence of pulsed radiation patterns having different orientations 165-r (discussed below). In some embodiments, birefringent phase retarders 166-k-i and 166-k-ii may be placed in front of each retro-reflector, their fast or slow axes aligned with the reflection symmetry axis of the corresponding retro-reflector 160-k, in order to rotate the polarization of the pulsed wavefront at the rate of pattern rotation. The thickness of each retarder 166-k may be chosen so that together with the retro-reflector 160-k, a half-wave relative phase retardance may be produced between the eigen-polarizations after each retro-reflection, resulting in an incremental tilt of the linear polarization axis by 2a upon each pass through the cavity, as illustrated on the Poincaré sphere 167.

Also illustrated are aspects of wavefront rotating using a pulsed laser mirror cavity system 860, in accordance with various embodiments. In this embodiment, a pulse of structured radiation 159-r, which may be produced by a laser, such as a Ti: Sapphire femtosecond laser merely by way of example, may be coupled into the cavity via a beam splitter 168-r through a hole in a curved mirror 169-r. A programmable grating 170-r, such as a Grating Light Valve (GLV) or a Surface Acoustic Wave (SAW) device, positioned near the center of the focal plane of the curved mirror 169-r may be used to diffract a fraction of the incident radiation 159-r in response to a control signal 171-r. The $1^{st}$ order diffracted radiation 172-r from the programmable grating may be focused by the curved mirror 169-r onto a retro-reflector 160-r-i/-ii positioned at a location near the center of the focal plane of the curved mirror 169-r. Other diffraction orders of the radiation may also be used in some embodiments. A retarder 166-r may be placed in front of the retro-reflector 160-r-i/-ii for polarization rotation as described earlier. The retro-reflected radiation may be directed once again onto the programmable grating 170-r. In response to the control signal 171-r, the programmable grating may diffract a portion 165-r of the incident radiation back through the hole in the curved mirror to be coupled out of the cavity via the beam splitter 168-r. Another portion 172-r of the incident radiation may be reflected by the programmable grating 170-r towards the curved mirror 169-r, which may focus the radiation reflected from the grating 170-r onto a second retro-reflector 160-r-ii whose reflection symmetry axis is tilted with respect to that of the first retro-reflector 160-r-i. Again, another retarder 166-r-ii may be placed in front of the retro-reflector 160-r-ii for polarization rotation. The retro-reflected radiation may be directed by the curved mirror 169-r onto the programmable grating 170-r and the process described above may be repeated multiple times, producing a sequence of rotated patterns 165-r at the cavity output. As illustrated, the grating control signal 171-r may vary in time such that an equal radiation intensity is coupled out of the cavity system 860 for each rotated pattern and the pulse energy within the cavity system 860 may be substantially depleted upon the full rotation of the pattern, at which point another radiation pulse may be coupled into the cavity system 860 as described above and the process repeats.

It should be apparent to those skilled in the art that a variety of implementations of the embodiment illustrated in FIG. 8 are possible within the spirit and scope of this invention. The retro-reflectors 160-r-i/-ii may be positioned at other locations within a mirror cavity system 860, such as the Fourier plane. The cavity system 660 may be unfolded such that a pair of lenses may be used instead of the curved mirror 169-r. In this case, a Bragg cell may be used instead of a programmable grating 170-r. The programmable grating 170-r or Bragg cell may also be used to spatially modulate the incident radiation 165-r to create a desired pattern, in which case the incident radiation may be unstructured. A passive wavefront rotation system can be designed in which the programmable grating 170-r may be replaced with a partially-reflecting mirror serving as both, an input and output coupler. In this embodiment, the beam splitter 168-r is not used and the incident wavefront 159-r enters the cavity through the coupling mirror. Furthermore, a gain medium may be added to the cavity system 860 to enhance its efficiency.

It should also be apparent to those skilled in the art that a variety of implementations of the embodiment in FIG. 8 are possible within the spirit and scope of this invention, including such variations as are seen with embodiments of FIGS. 1-7. Furthermore, various components of FIG. 8 may be labeled with first reference numbers that may be described above along with FIGS. 1, 2, 3A, 3B, 4, 5, 6, and 7. A second reference label on a component may merely reflect that the component is part of a specific figure.

Figure 9:
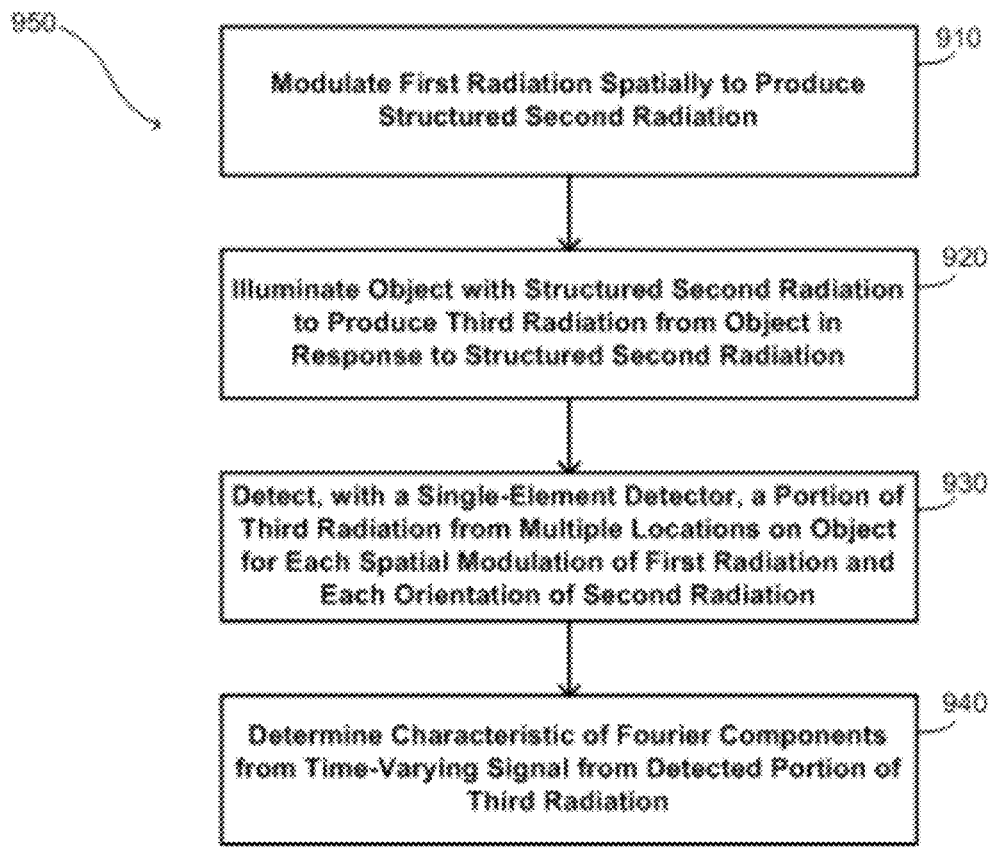
FIG. 9 is a flowchart of a method of measuring one or more sinusoidal Fourier components of an object, in accordance with various embodiments.

FIG. 9 is a flow chart illustrating a method 950 of measuring one or more sinusoidal Fourier components of an object. The method 950 may, for example, be performed in whole or in part within the systems of FIGS. 1-8. Further aspects and additional embodiments of method 950 may be more thoroughly discussed within the description provided within these systems and are thus not necessarily repeated here.

At block 910, a first radiation is spatially modulated resulting in a structured second radiation. Spatially modulating the first radiation utilizes a variety of different modulators including, but not limited to, a one-dimensional acousto-optic Bragg cell, a multi-dimensional acousto-optic Bragg cell, a surface acoustic wave device, a programmable grating device, a liquid crystal array, or a digital micromirror device. In some embodiments, spatially modulating the first radiation may be along multiple non-parallel directions. Spatially modulating the first radiation may depend on the object and/or a structure of the structured second radiation.

The first radiation may be visible and/or invisible, particulate and/or wavelike, and may be temporally and/or spatially coherent, as in the case of laser radiation, and/or partially coherent, as in the case of radiation from a Light Emitting Diode (LED). In some embodiments, the first radiation may have a spectral distribution, such as a broadband radiation. A first radiation with spectral distribution may be partially spatially coherent. The first radiation may be pulsed in some embodiments. The first radiation may be amplitude modulated in time in some embodiments. Spatially modulating the first radiation may also include phase modulation, polarization modulation, and/or amplitude modulation. The spatial modulation may be along a single direction or along multiple directions.

In some embodiments, generating the second structured radiation may be controlled to reduce errors in the structured second radiation. The relative strengths of the sinusoidal Fourier components of the structured second radiation may be varied in some embodiments. In some embodiments, spatial frequencies present in the structured second radiation may be non-redundant.

At block 920, the object is illuminated with the structured second radiation to produce a third radiation from the object in response to the illuminating. The structured second radiation may be scaled and oriented relative to the object. Orienting the second radiation relative to the object may include orienting the structured illumination relative to a reference frame. Orienting the second radiation relative to the object may include orienting the object relative to a reference frame. A reference frame may be defined by a Fourier domain sensing system within which method 950 may be implemented.

At block 930, a single-element detector detects a portion of the third radiation from multiple locations on the object simultaneously for each spatial modulation of the first radiation and for each orientation of the second structured radiation. The third radiation may include radiation that is scattered, reflected, transmitted, fluoresced, and/or otherwise generated by the object.

In some embodiments, multiple single-element detectors may be used, wherein each of the single-element detectors detects a portion of the third radiation from multiple locations on the object. The detected portion of the third radiation detected by each of the multiple single-element detectors may have a substantially different wavelength and may be due to substantially different Fourier components of the object than radiation detected by one or more other the single-element detectors.

In some embodiments, the phase of one or more sinusoidal Fourier components of the spatial modulation may be changed between multiple successive detection times. The spatial frequency of one or more sinusoidal Fourier components of the spatial modulation may be changed between multiple successive detection times. The orientation of the structured second radiation with respect to the object may be changed between multiple successive detection times. The strength of one or more sinusoidal Fourier components of the structured second radiation may be changed between multiple successive detection times.

At block 940, characteristics of the sinusoidal Fourier components of the object are estimated based on a time-varying signal from the detected portion of the third radiation. The characteristics may include a phase, a weighted sum of the phases, an amplitude, or a weighted sum of the amplitudes of the sinusoidal Fourier components of said object, merely by way of example.

In some embodiments, method 950 may also include reconstructing an image of the object. The image may be reconstructed from the measured sinusoidal Fourier components of the object. The image may be one dimensional, two dimensional, or three dimensional. In some embodiments, reconstructing an image of the object may involve a direct Fourier transformation of the measured Fourier components of the object. In some embodiments, depth of field and resolution of the image may be substantially decoupled. The resolution of the reconstructed image may surpass the diffraction limit of the optical system receiving the radiation from the object. In some embodiments, geometrical parameters of the object, such as position, orientation, and scaling, may also be determined from the measured Fourier components.

In some embodiments, method 950 may also include calculating at least one projection of the objected based on the time-varying signal. From the projections, an image may be reconstructed in some embodiments by applying a tomographic filtered backprojection algorithm to one or more projections.

In some embodiments, method 950 may also include synthesizing a structure or image of the object by illuminating a recording medium with a sequence of radiation patterns. Each radiation pattern may include one or more characterized Fourier components. The recording medium may include a variety of media including, but not limited to, a bias-subtracting detector array, a photorefractive crystal, or a photoresist.

In some embodiments, method 950 may include estimated characteristics of sinusoidal Fourier components of the object that may form a sparse subset of a Fourier basis set of the object. The sparse subset may be chosen to efficiently image a class of objects and/or to better utilize the information throughputs and/or capacities of the optical, electronic, and/or processing systems. In some embodiments, the object may be classified based on characteristics of the sinusoidal Fourier components of the object. In some embodiments, the classification maybe made by using structured illumination that includes Fourier components of a matched filter.

In some embodiments, method 950 may also include modulating the time-varying detected signal onto a carrier signal having a substantially fixed frequency by electronically mixing the time-varying detected signal with a time-varying reference signal. Some embodiments may include modulating the structured second radiation with a time-varying reference signal to produce the time-varying detected signal having a substantially fixed frequency within a bandwidth of the detector. Modulating the structured second radiation may include amplitude, frequency, phase, and/or polarization modulation.

Figure 10:
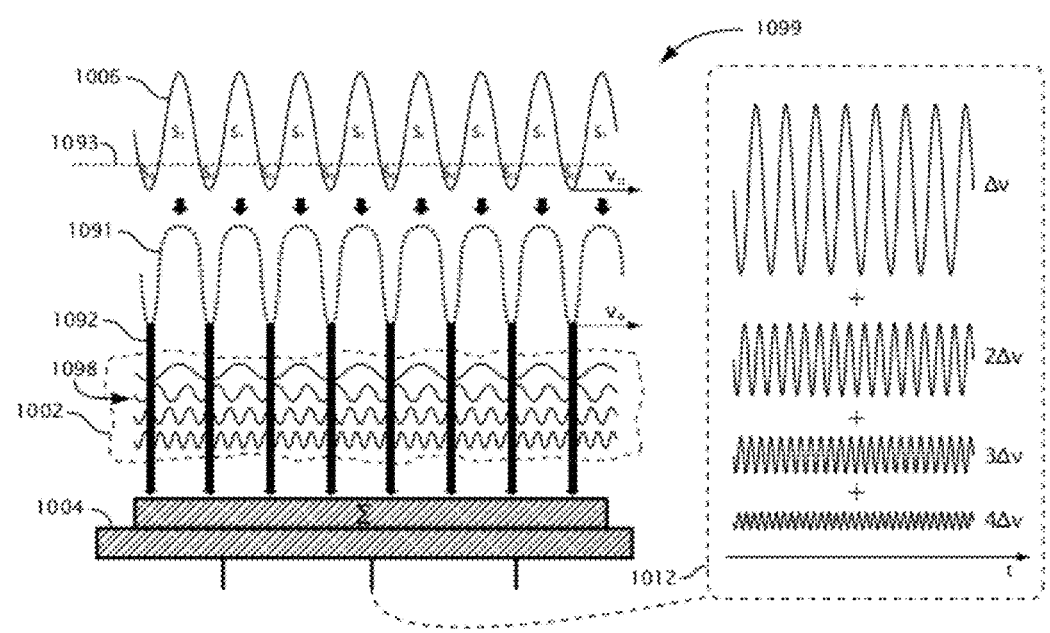
FIG. 10 illustrates an nonlinear response to traveling structured illumination intensity due to molecular-level saturation in which nearly all molecules are in an excited state or in a dark state resulting in a detector signal that probes multiple harmonic spatial Fourier components, thereby enabling resolution beyond the classical diffraction limit.

The effect of an incoherent nonlinear response to a traveling high-intensity illumination pattern is illustrated with FIG. 10, which by way of example schematically shows the spatially-varying saturable fluorescence response 1091 of an object 1002 to an intensity pattern 1006 on the left portion of the drawing, and the resulting compound signal 1012 obtained by a spatially-integrating detector 1004 on the right portion of the drawing. This incoherent nonlinear interaction results from saturation on a molecular level such that nearly all molecules are either in an excited state or in a "dark" state within a region where the illumination intensity exceeds a saturation threshold $I_s$ 1093. When the illumination intensity 1006 exceeds the saturation threshold $I_s$ 1093, fluorescence begins to saturate and grow nonlinearly with intensity. For high intensities, in regions where $I_i<I_s$, almost all fluorophores are in the "dark" state, whereas in regions where $I_i>I_s$, almost all fluorophores are excited, thereby "squaring up" the effective excitation pattern and the resulting response 1091. As the resulting narrow "dark stripes" 1092 of no fluorescent response move across the object 1002, the spatially-integrated intensity generates a detector signal 1012 comprising multiple harmonics, thereby probing multiple corresponding harmonic Fourier components 1098 of the object simultaneously and making it possible to probe features below the diffraction limit that would be unresolvable with a linear system. The intensity of the signal falls with frequency even if the Fourier spectrum of the object 1002 is flat since the width of the dark stripes 1092 increases relative to the spatial period, resulting in a larger integration window. The same result is obtained by Fourier transformation of the emission intensity 1091. It is also possible to reverse the situation by using a periodic depletion intensity pattern to quench nearly all fluorescence in regions where $I_i>I_s$. In this case, narrow "bright stripes" of fluorescence corresponding to the darkest regions of the depletion pattern would move across the object 1002, producing an analogous time-varying detector signal 1012.

These methods differ from other super-resolution methods based on a nonlinear response to high-intensity illumination that rely on conventional imaging using a detector array or on scanning a tightly-focused beam or beams across the object. Saturable fluorescence structured illumination microscopy employing a sequence of sinusoidal illumination patterns with different phases and orientations has been used to resolve ~50 nm fluorescent beads using five detectable excitation harmonics, for example. Moreover, several related saturation schemes, sometimes collectively referred to as "far-field optical nanoscopy," have been used to attain resolutions on the order of ~10 nm with a scanning far-field microscope using conventional optics. With sufficient illumination power, many such nanoscopy techniques, as well as other incoherent nonlinear processes such as saturable absorption, are compatible with methods of the invention. Scanning Stimulated Emission Depletion ("STED") microscopy, for example, combines a focused excitation beam at one wavelength and a depletion beam with an annular focal spot at a different wavelength to quench fluorescence everywhere except for a small central region much smaller than the diffraction-limited PSF. According to the methods of the invention, on the other hand, a 1D intensity profile (which could be sinusoidal or not, depending on the modulation signal) could be used instead of the donut-shaped depletion beam. One of the challenges in scanning-spot STED lies in rapidly translating the depletion beam with resolution-scale precision (e.g. ~10 nm). According to embodiments of the present invention, however, scanning in 1D is accomplished automatically with high speed and precision by the moving interference pattern. Furthermore, the saturable fluorescence response can be measured while maintaining other benefits of the invention described herein such as extended depth of field, high-speed three-dimensional Fourier measurements, deeper imaging in scattering media, and large-working distance microscopy.

Figure 11:
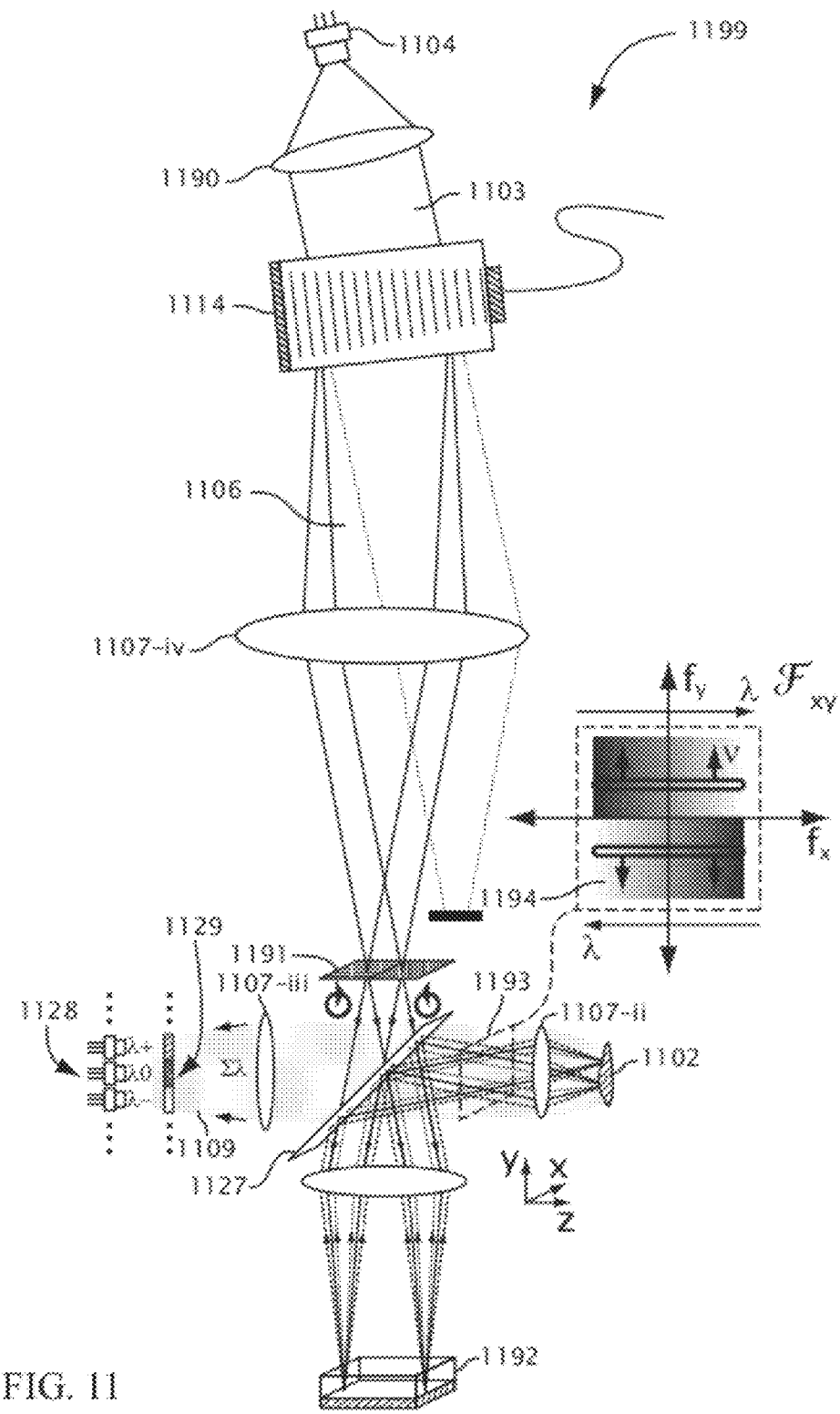
FIG. 11 illustrates a system for implementing Fourier-plane wavelength encoding of the structured illumination and spectral de-multiplexing using wavelength-selective detectors, thereby increasing measurement parallelism and acquisition speed.

In addition to temporal frequency multiplexing, another level of parallelism may be obtained by wavelength-encoding the illumination in a Fourier plane and using an array of wavelength-selective detectors, thereby further speeding up measurement of scattering objects. FIG. 11 illustrates one way to measure the entire two-dimensional Fourier space of the object using a single one-dimensional frequency scan without rotating the object 1102 or the structured illumination 1108. The system is identified generally by reference number 1199. In this case, a broadband source 1104 of radiation 1103 is used and a specially designed hologram 1192 is used to disperse in opposite directions partially coherent illumination beams 1106 so that opposite sides of the Fourier plane 1193 have a mutually-reversed and centrosymmetric wavelength mapping 1194. This is accomplished in a specific embodiment using a highly angle-selective hologram or alternatively by encoding the opposing illumination beams with orthogonal polarizations using a split polarization element 1191 near a Fourier plane, for example, and employing a polarization-selective hologram 1192. A polarization analyzer at the detector or at the object may then be used to ensure good interference contrast. The multispectral response 1109 from a scattering object 1102 may be demultiplexed using multiple detectors 1128 placed behind an array 1129 of spectral filters or by dispersing the scattered light onto a detector array using a grating, for example. Merely by way of example, the drawing shows optical elements, including lenses 1107 and a beam splitter 1127, that may be used to direct the broadband radiation 1103 collimated using a lens 1190 and spatially-modulated by an acousto-optic Bragg cell 1114 onto the dispersive hologram 1192 and the object 1102 and collecting the object's response 1109 onto an array of wavelength-sensitive detectors 1128. When combined with RF frequency multiplexing, Fourier-plane wavelength encoding may be used to measure the entire two-dimensional Fourier space of the object during a single Bragg cell access time (e.g. ~20 μs).

Figure 12:
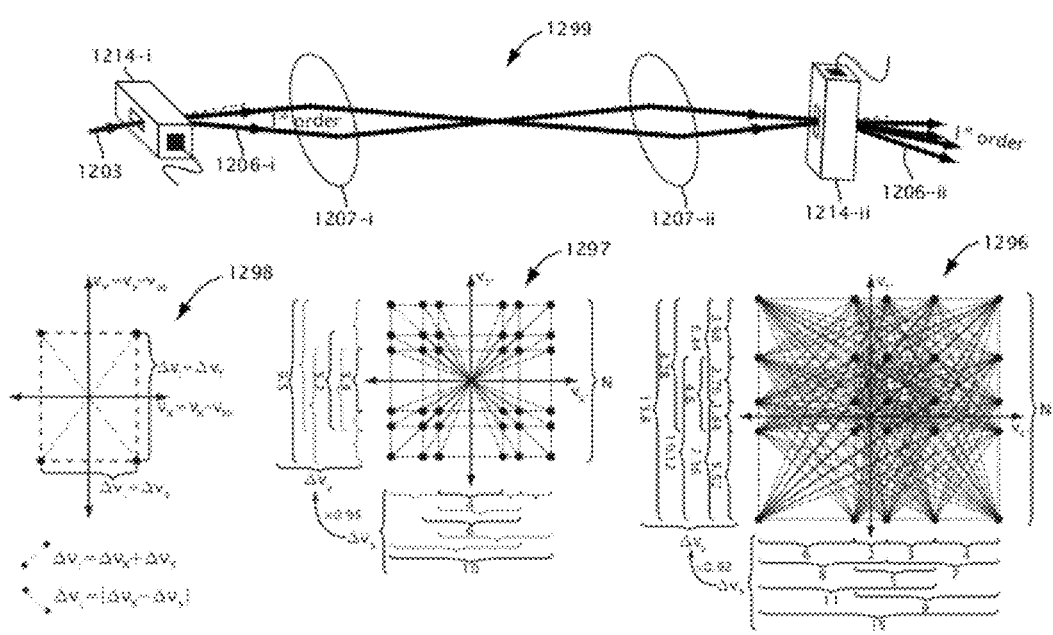
FIG. 12 illustrates a system for generating dynamic multi-dimensional illumination patterns using crossed acousto-optic Bragg cells and various redundant and non-redundant frequency multiplexing schemes enabling high-speed parallel measurement of the object's Fourier space.

Moving mechanical components, such as a prism used to rotate the illumination in some embodiments, may limit data acquisition speed and may adversely affect the accuracy of the Fourier measurements. One approach that obviates moving components and may therefore greatly enhance acquisition speed and improve measurement precision employs two-dimensional acousto-optic diffraction to generate multi-dimensional dynamic frequency-multiplexed illumination patterns either by using a single two-dimensional Bragg cell (which typically comprises a stack of two orthogonally cut crystals, each driven by a separate transducer), or by using two orthogonally oriented one-dimensional Bragg cells placed in conjugate optical planes as illustrated by system 1299 in FIG. 12. In the case of sequential Fourier sampling, for example, an input 1203 is diffracted by the first Bragg cell 1214-*i* to generate two first-order beams 1206-*i* that are directed by lenses 1207 to be used as inputs to the second Bragg cell 1214-*ii*. To ensure that the diffracted beams can be made to rotate about a common center and can sample frequencies anywhere in the Fourier plane down to DC, the second Bragg cell 1214-*ii* is also driven with two tones, resulting in four diffracted first-order beams 1206-*ii* that map to four points in RF frequency space 1298.

The four distinct interference patterns due to the diagonal, horizontal, and vertical beam pairs map to unique RF carriers in the detector signal, so that four distinct spatial Fourier components can be measured simultaneously. Note that the vertical frequency spacing should be different from the horizontal frequency spacing to avoid a stationary interference pattern contribution along one of the diagonal directions. Thus, by separately controlling the difference frequencies of the two-tone signals driving each Bragg cell 1214, it is possible to scan the entire two-dimensional Fourier space, measuring four frequency samples at a time.

Two-dimensional acousto-optic scanning can also leverage frequency multiplexing to speed up the measurement and improve the SNR ever further. For example, space 1297 shows a two-dimensional double-sided non-redundant sampling scheme that can be used to measure multiple separable in-plane Fourier components at once (24 in this case) with a strategic choice of drive frequencies. In this example, the same frequency pattern is used to drive the orthogonal Bragg cells, however the frequency scaling is chosen to be slightly different along the two axes to maximize the number of non-redundant carriers in the detector signal. Note, however, that the patterns along the $v_{X'}$ and $V_{Y'}$ axes do not have to be the same (to a scale factor), as long as both 1D patterns are double-sided non-redundant. It can be concluded from symmetry considerations that only those diagonal frequency pairs that are symmetric about the origin can produce signals with unique RF carriers. Furthermore, as in the sequential case, horizontal and vertical beam pairs contribute strong degenerate interference patterns, probing additional in-plane Fourier components. Thus, using this scheme it is possible to measure up to $N^2/2+N$ separable in-plane Fourier samples at once (where N is the number of frequencies in each drive signal). On the other hand, signals due to redundant tilted illumination patterns produced by off-axis diagonal beam pairs can be rejected by filtering to attain a large DOF, but at the cost of signal loss.

A more light-efficient approach that is particularly well suited for tomographic 3D imaging is the non-planar non-redundant Fourier sampling scheme shown in space 1296. In this case, the drive frequencies can be chosen such that every possible diagonal beam pair (there are 200 in all for the array shown) produces a signal at a distinct RF frequency. In the illustrated example, this is accomplished by using the same non-redundant pattern along $v_{X'}$ and $V_{Y'}$ axes, but choosing a slightly different frequency scaling factor for each axis to ensure that the diagonal frequency differences are non-redundant and sufficiently separated from each other. Moreover, as before, horizontal and vertical beam pairs result in strong degenerate in-plane interference patterns that probe additional in-plane Fourier coefficients (10 in the illustrated example). This massively parallel scheme makes it possible to probe $$\frac{N^2(N-1)^2}{2} + 2\binom{N}{2}$$

individual Fourier components simultaneously and to populate hundreds (or, for larger arrays, perhaps even thousands) of individual points in the 3D Fourier space during a single Bragg cell access time without signal loss. In the example case of the illustrated 5×5 array where the vertical frequency pattern is a scaled version of the horizontal one, 210 separable signals are obtained with a minimum carrier separation of 0.04 in the arbitrary frequency units used. Although the inter-relationship between the measured locations cannot be chosen arbitrarily, by scaling the frequencies and using several different non-redundant array patterns, it should be possible to attain good coverage of the 3D Fourier space.

Figure 13:
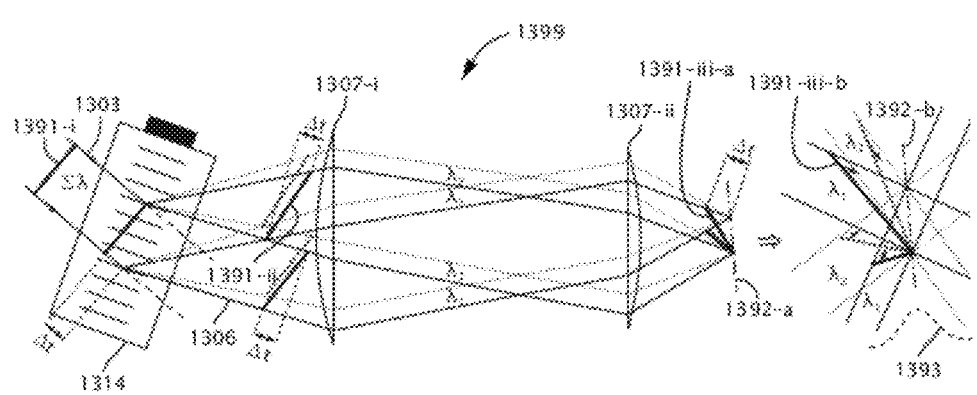
FIG. 13 illustrates a system that employs temporal focusing of pulsed illumination, thereby providing axial resolution.

An embodiment of the invention that employs temporal focusing of pulsed broadband illumination and provides axial resolution is illustrated with FIG. 13. In this drawing, the system is denoted generally by reference number 1399. An uncompensated broadband pulsed beam 1303 is incident on a Bragg cell 1314, which introduces a time delay across each diffracted first-order spectral component 1306 such that the dispersed coherent pulse fronts 1391 directed by lenses 1307 coincide temporally only at the focal plane 1392 (this results in a rapid line scan across the focal plane over the duration of the pulse). Away from the focal plane, the dispersed wavefronts combine increasingly incoherently and the pulse rapidly broadens with defocus. In the case of a multiphoton fluorescent response, for example, since efficient excitation occurs only when the peak photon density is high, this effectively limits the multiphoton excitation depth to a narrow 2D slice of the focal volume, whereas background two-photon fluorescence from outside the focal plane is suppressed.

Moreover, each spectral component of the dispersed first-order beams results in a sinusoidal interference pattern at the focal plane. Although the spatial frequency of the interference patterns is common across the entire spectrum, due to angular dispersion which maps to a time delay introduced by the tilted Bragg cell 1314 across each diffracted beam, the spectral component interference patterns combine increasingly out-of-phase with defocus, resulting in an interference contrast function 1393 that peaks at the focal plane 1392. The loss of interference contrast and broadening of the pulses are due to the same phenomenon—loss of phase coherence across the spectrum with defocus. Thus, axial resolution is obtained even for a CW broadband source due to the limited coherence depth. However, the out-of-focus regions with low interference contrast contribute DC background to the detector signal, reducing the signal-to-noise ratio. With a femtosecond pulsed source, on the other hand, in out-of-focus regions where the interference contrast is low, the interfering pulses are also temporally broadened, which greatly reduces two-photon emission. As a result, out-of-focus background emission (and photodamage) is suppressed, resulting in true two-photon axial sectioning. The focal plane of temporal coincidence and multispectral coherence can be scanned in depth by controlling the second-order group delay dispersion of the incident pulse using a pulse compressor, for example.

Figure 14:
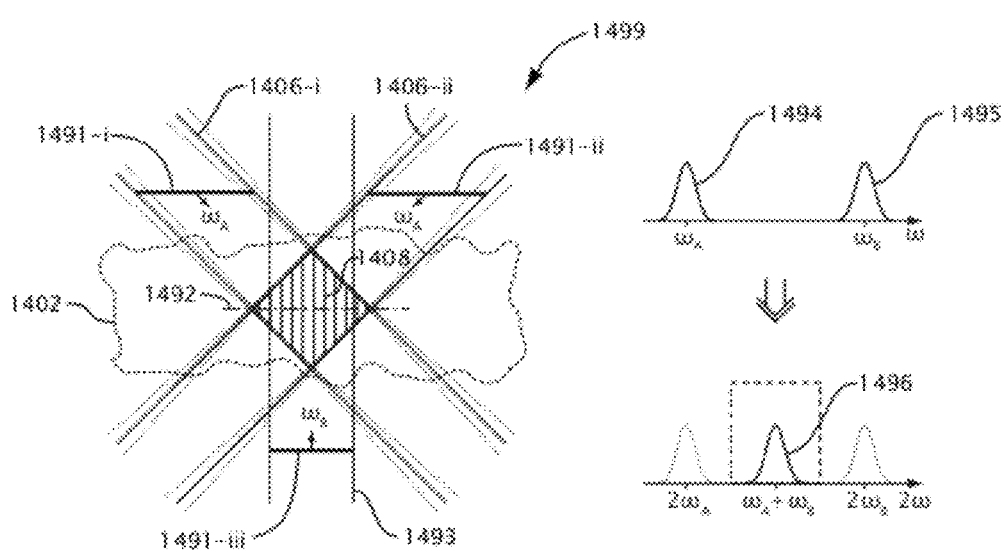
FIG. 14 illustrates a system using spectrally-diverse pulsed illumination that may be used to probe nonlinear contrast within a narrow depth slice.

FIG. 14 illustrates an embodiment of the invention that may advantageously be used to probe nonlinear contrast within a narrow depth slice while minimizing photodamage. The system is denoted generally by reference number 1499. A thin, mostly transparent sample 1402 is illuminated with a pair of femtosecond pulses 1406-i and 1406-ii and a third synchronous counter-propagating femtosecond pulse 1493 is introduced such that the three coherent pulse fronts 1491 overlap temporally only within a narrow focal plane 1492. By arranging (e.g by using a pulse-shaper) that the counter-propagating pulse 1493 spans a different wavelength range than the other two pulses 1406, as illustrated by the excitation spectra 1494 and 1495, it is possible to ensure that a two-photon signal at the sum frequency is produced only when all three pulses overlap, as illustrated by the two photon emission spectrum 1496. Although the illustrated beams are dispersion-compensated and therefore exhibit co-planar pulse fronts, this approach is also compatible with the temporal focusing arrangement described above where the interfering pulses result in a rapid line-scan of the focal plane. However, in this case, the dispersion of the counter-propagating beam 1493 is adjusted such that its pulse front scans the focal plane 1492 synchronously with the other two beams.

Unlike temporal focusing, with this approach, axial-sectioning resolution is determined by the temporal width of the femtosecond pulses rather than by Bragg cell dispersion. For example, a 50-fs pulse results in an 11-μm depth resolution in water. Moreover, the focal plane can be tuned in depth by adjusting the relative timing between the counter-propagating pulse 1493, such as by using a piezoelectrically scanned mirror. Since the interference pattern 1408 is due to the two co-propagating beams 1406 generated using a common-path interferometer, the third beam 1493 does not need to be interferometrically stable. Pulse wavelength diversity used in the three-pulse axial sectioning scheme could also be helpful in conjunction with temporal focusing in the two-beam configuration. Since two-photon fluorescence at the sum frequency

1496 can occur only when the interfering pulse fronts coincide temporally, this constitutes another depth-gating constraint in addition to temporal focusing of the individual pulses.

Figure 15:
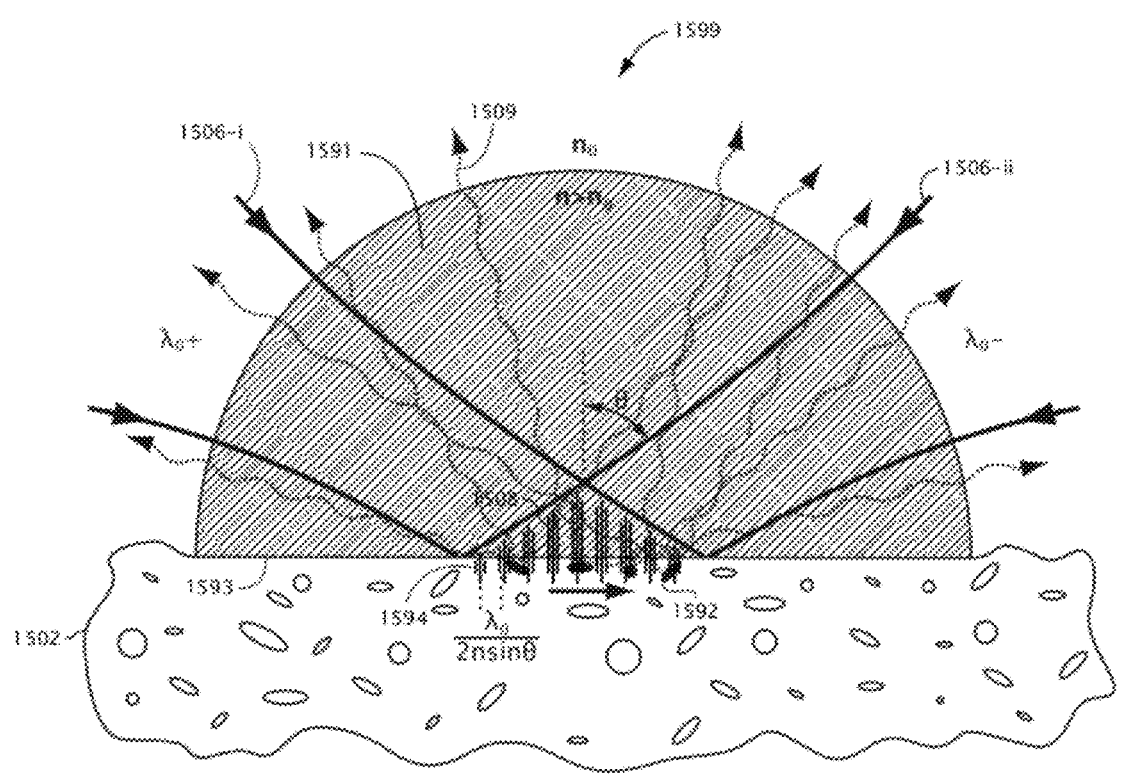
FIG. 15 illustrates a system for super-resolved imaging that relies on near-field probing of a surface of an object.

FIG. 15 illustrates a linear technique for super-resolution imaging that relies on near-field probing of fine-scale features 1592 near a surface 1593 of an object 1502. The system is denoted generally by reference number 1599. The illumination beams 1506 are made to interfere inside a high-index material 1591 such as Si or $LiNbO_3$, producing higher-frequency dynamic interference patterns than would be possible in air. The resulting near-field excitation 1594 decays exponentially at the interface of the material, exciting only those fluorophores 1592 in the sample 1502 that lie in very close proximity to the interface. A circularly and radially symmetric high-index "lens" may enable wide-field super-resolution two-dimensional imaging in the near field. With sufficiently narrow illumination beams 1506, the shape of the high-index lens 1591 may be spherical.

This approach is similar to using an oil-immersion objective to achieve a super-unity numerical aperture, but since the signal is due to a near-field interaction and the light 1506 does not need to penetrate into the sample 1502, much-higher index materials can be used. For example, a silicon "lens" 1591 with an index of ~4 may be used to attain up to ~100-nm lateral resolution with 800-nm illumination (alternatively, the high-index lithium niobate or diamond materials could be used with visible light to attain similar resolutions). Whereas with conventional free-space lens-based optics it is difficult to attain a sharp point-spread-function inside such high-index materials over a wide field, embodiments of the invention enable wide-field sinusoidal interface patterns 1508 to be generated inside the high-index material 1591 sequentially for each measured spatial frequency and to be phase-cohered during synthesis (or electronically during acquisition). As long as the interfering beams 1506 are narrow enough that the phase gradient across each beam is approximately linear, aberrations at the air interface can be fully compensated. Since the evanescent waves 1594 decay rapidly into the sample 1502, the large depth-of-field capabilities are not relevant in this case since only structures within ~100 nm of the near-field interface are probed.

This near-field "axial sectioning" effect is leveraged in the established Total Internal Reflection Fluorescence ("TIRF") microscopy technique, where a wide evanescent field produced due to the total internal reflection of a plane wave launched inside a material with a higher index than the sample (e.g. a glass coverslip) is used to study small-scale processes and structures at the near-field interface and eliminate background fluorescence from the rest of the sample. Unlike TIRF-based techniques, with embodiments of the invention, no imaging is necessary after the sample is excited by the evanescent field and the fluoresced light 1509 can be measured from the illumination side through the same high-index material used for excitation. Near-field resolution may be increased further by combining this technique with wide-field multi-photon fluorescence excitation as well as with nonlinear super-resolution methods.

Figure 16A:
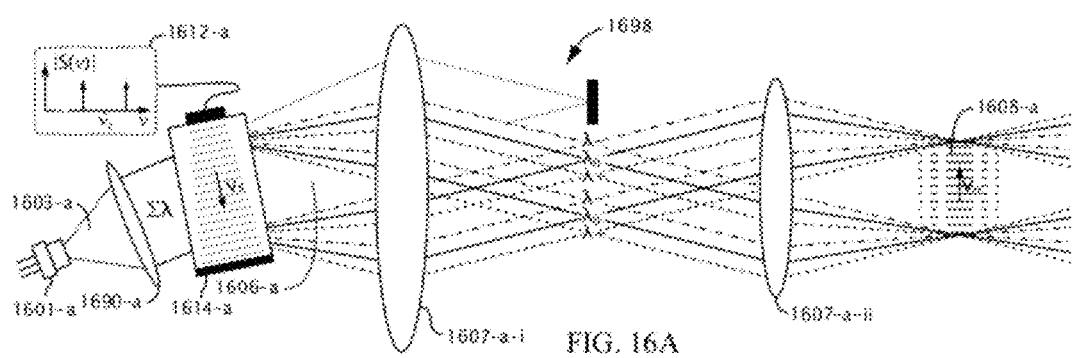
FIG. 16A illustrates the use of broadband radiation to limit the depth of field and increase axial resolution.

FIG. 16A illustrates a system in which broadband radiation may limit the depth of field and increase axial resolution in accordance with some embodiments of the invention. The system is denoted generally by reference number 1698. In this configuration a broadband source 1601-$a$ generates radiation 1603-$a$ collimated by a lens 1690-$a$ and directed to be incident on a Bragg cell 1614-$a$ driven with an electrical signal with a two-tone RF spectrum 1612-$a$. For a resultant pair of interfering beams 1606-$a$, since the linear variation of the Bragg diffraction angle with wavelength opposes the wavelength dependence of the wave vector of each beam, the period of the interference pattern 1608-$a$ illuminating the object after passing through lenses 1607-$a$ is independent of wavelength. Moreover, since the phase of a monochromatic interference pattern at the object plane depends on the acoustic phase rather than the optical phase of the source, all component monochromatic interference patterns combine in-phase. As a result, the object is illuminated with a high-contrast broadband interference pattern characteristic of a common-path grating interferometer (neglecting any gradual wavelength dependence of Bragg diffraction efficiency). Note that if the broadband light source is used to directly illuminate the Bragg cell as illustrated, each incident spectral component is diffracted by the Bragg cell at a slightly different angle. This angular dispersion at the Bragg cell is responsible for a wavelength-dependent tilt of the interference patterns due to each spectral component in object space, resulting in spectral de-phasing and loss of broadband interference contrast with defocus.

Figure 16B:
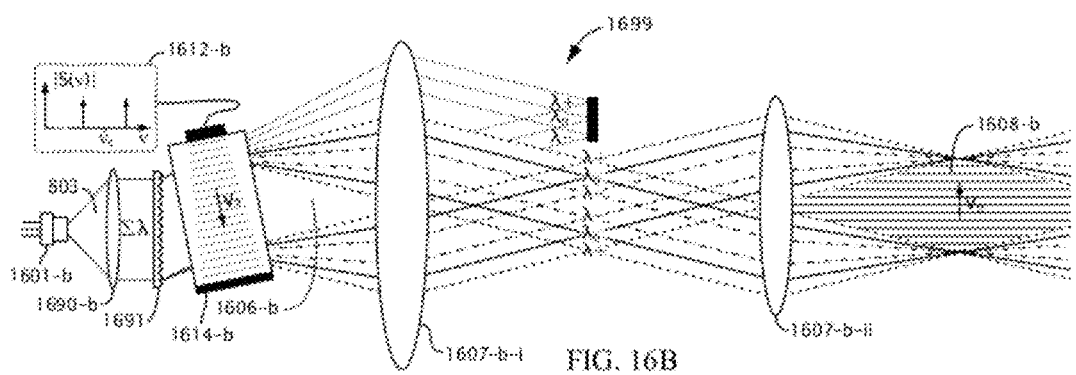
FIG. 16B illustrates the use of linear dispersion compensation to attain a large depth of field using broadband illumination.

While this effect can be useful in attaining axial sectioning with some embodiments of the invention, it can also be counteracted to maintain an extended broadband depth of field by introducing a dispersion-compensating element (e.g. an appropriately-chosen grating) before the Bragg cell, as illustrated by the system denoted generally by reference number 1699 in FIG. 16B. In this configuration a broadband source 1601-$b$ generates radiation 1603-$b$ collimated by a lens 1690-$b$, diffracted by a dispersive element 1691, and directed to be incident on a Bragg cell 1614-$b$ driven with an electrical signal with a two-tone RF spectrum 1612-$b$. The dispersive element ensures that the angle of incidence at the Bragg cell varies with wavelength such that when the RF difference frequency is zero, all $1^{st}$ order diffracted spectral components are co-aligned. This makes it possible to attain a depth of field with broadband illumination that is nearly as large as in the monochromatic case, which can be advantageous in some embodiments of the invention.

Figure 17:
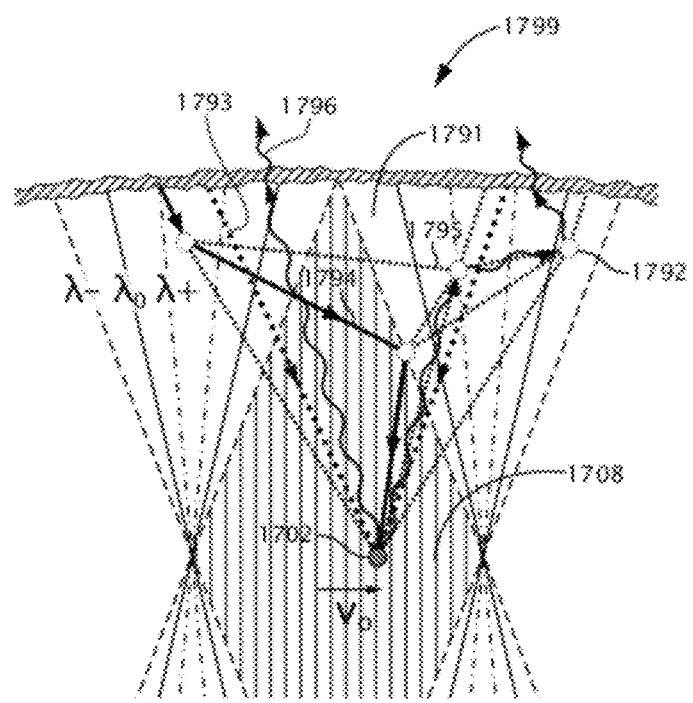
FIG. 17 illustrates increasing the imaging depth in scattering media such as biological tissue through wide-field structured illumination coherence gating.

As illustrated in FIG. 17, by using a broadband light source, it may also be possible to increase the imaging depth in scattering media such as biological tissue through wide-field structured illumination coherence gating. The system is denoted generally by reference number 1799. When a scattering medium is illuminated with a broadband interference pattern, ballistic photons (dotted lines) produce high-contrast fringes at the spatial frequency being measured, whereas various scattering paths (thin lines) contribute an unwanted distribution of spatial frequencies. However, differences in optical paths (e.g. arrowed lines) that exceed the light source coherence length produce only weak intensity modulation at the detector, resulting in improved ballistic signal visibility. Light scattered or fluoresced by the object (wavy lines) in response to the moving fringes, can take any path out of the scattering medium and contributes to the signal as long as it is detected.

When a scattering medium 1791 is illuminated with a broadband interference pattern 1708, ballistic photons 1793 produce high-contrast fringes at the spatial frequency being measured, whereas various scattering paths 1795 contribute an unwanted distribution of spatial frequencies. However, analogously to Optical Coherence Tomography ("OCT") and according to embodiments of the invention, scattering-induced changes in a photon's optical path 1794 exceeding the temporal coherence length of the illumination suppress the contrast of interference involving that photon (the photon loses phase coherence with photons of other wavelengths), producing only weak intensity modulation at the detector and resulting in improved ballistic signal visibility. According to embodiments of the invention, the coherence-gated interference contrast occurs in the spatial domain at the object 1702 rather than in the temporal domain at the detector as in OCT. As a result, temporal coherence gating may occur over the entire field of view simultaneously, whereas OCT relies on spatial scanning to build up the three-dimensional image. In various embodiments, the wide-field structured illumination coherence gating effect may be leveraged in conjunction with any of the broadband tomographic and axial sectioning techniques (linear and nonlinear) described above.

In time-domain OCT, the signal measures the contrast of the interference at the detector of back-scattered photons from the object with a reference beam as the reference path length is scanned. As a result, photons that traverse a longer (or shorter) path than the reference beam are filtered out so that only signal from scatterers 1792 located at the depth corresponding to that of the reference mirror remains. Since in OCT it is not possible to distinguish between photons that are scattered before hitting the intended target and those that are scattered on their way back to the detector, multiply scattered illumination and response photons are both rejected by coherence gating. In embodiments of the invention, conversely, only the illumination photons are coherence-gated while the response signal photons are spatially integrated before detection and hence can take any path 1796 through and out of the scattering medium 1791. The inventors conjecture that this may lead to higher light efficiency, potentially doubling the imaging depth of the technique compared to OCT.

Another distinction between OCT and embodiments of the invention is that the latter are sensitive to both fluorescent and scattering objects 1702, whereas OCT is a coherent technique that is sensitive only to scattering structures. This may enable wide-field three-dimensional imaging of fluorescence contrast in scattering media such as biological tissue at depths similar to those accessible by OCT.

Figure 18:
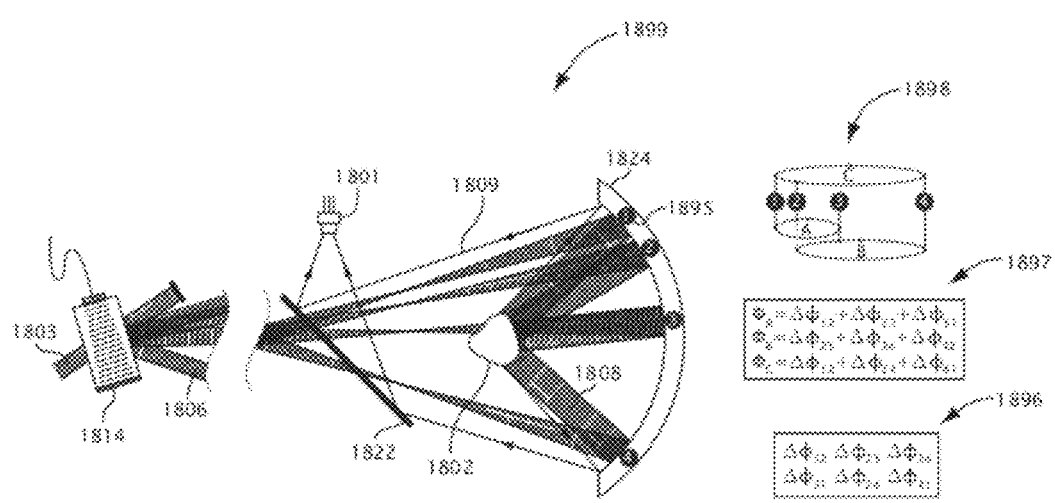
FIG. 18 illustrates a system that uses closure phases formed from non-redundant Fourier measurements to provide additional constraints for phase error compensation.

FIG. 18 illustrates a system that uses closure phases formed from non-redundant Fourier measurements to provide additional constraints for compensating differential phase errors due to a large low-precision optical surface. The system is denoted generally by reference number 1899.

Phase closure algorithms were initially developed by radio astronomers to phase-cohere disparate antenna elements and later extended to infrared and optical interferometry to compensate for atmospheric and telescope phase errors across the receiving aperture. These techniques rely on the concept of a "closure phase" obtained by summing the relative phase measurements due to each elemental pair in a closed loop of interferometer antennas (or openings in an aperture mask). Each closure phase thus obtained depends only on the intrinsic relative phases measured by the antenna elements and is insensitive to local phase offsets (e.g. due to atmospheric fluctuations or telescope errors) at each antenna.

$$\binom{N-1}{2}$$

independent closure phases can be obtained for a non-redundant array with N elements (e.g. by choosing an antenna element and finding all three-element loops that contain it). However, since such an array probes $$\binom{N}{2}$$

different Fourier pairs, closure phases alone are not enough to eliminate all phase errors. Instead, closure phases can be used as additional constraints in iterative techniques such as the well known CLEAN algorithm. As the size of the non-redundant array is increased, the number of independent closure phases approaches the number of unknowns (e.g. closure phases alone carry 96% of the phase information for a 50-element array), leading to faster and more accurate convergence of the iterative algorithm. Moreover, if redundant Fourier pairs are introduced, it is possible to remove phase errors algebraically without constrained optimization.

As in aperture mask interferometry, the synthetic aperture 1824 of a system 1899 in accordance with embodiments of the invention can be treated as an array 1898 of antenna elements 1895 (except that each pair of elements is used to transmit an interference pattern rather than detect one). In non-redundant frequency measurements, each pair of illumination beams 1808 probes a different Fourier component of the object 1802 and produces a signal at a distinct carrier frequency at the detector 1801. Merely by way of example, system 1899 shows an embodiment where radiation 1803 incident on a Bragg cell 1814 to generate modulated illumination 1806, which is directed to the object 1802 with a curved mirror 1824, whereas the object's coherent or incoherent response 1809 is directed to the detector 1801 via a beam splitter 1822. Closure phases 1897 formed from the Fourier phase measurements can be used as additional constraints (for constrained iterative optimization techniques, for example) to solve for the unknown intrinsic differential phases 1896 and correct for phase errors due to the large low-precision optical surface 1824.

Figure 19:
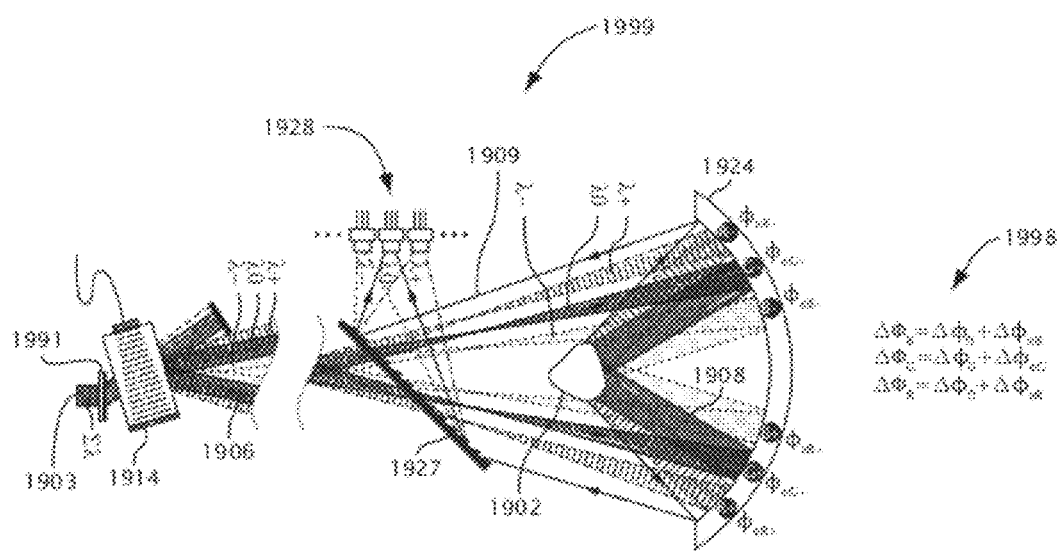
FIG. 19 illustrates a system that uses degenerate Fourier measurements at multiple wavelengths to provide additional constraints for phase error compensation.

FIG. 19 illustrates a system that uses degenerate Fourier measurements at multiple wavelengths to provide additional constraints for phase error compensation. The system is denoted generally by reference number 1999. Dispersion-compensated broadband reflective embodiments of the invention can be used to measure a given Fourier component of the object 1902 using a spectrum of wavelengths. Due to angular dispersion at the Bragg cell 1914, which receives radiation 1903 spectrally separated by grating 1991, each spectral component of the modulated radiation 1906 is affected by differential phase error at a distinct radius on the aperture 1924 before the illuminating radiation 1908 produces interference patterns at a scattering object 1902. By spectrally separating the response signal 1909 with a dispersive element 1927 such as a grating and detecting it with an array of detectors 1928 (or alternatively, an array of spectrally filtered detectors or a sequence of spectral filters in front of a single detector could be used, for example), it is possible to generate a set of equations 1998 that could be used as an additional constraint for iterative phase estimation algorithms. Moreover, by combining these cross-spectral measurements with closure phases, it is possible to directly solve for the phase errors across the aperture without the use of array redundancy.

Figure 20A:
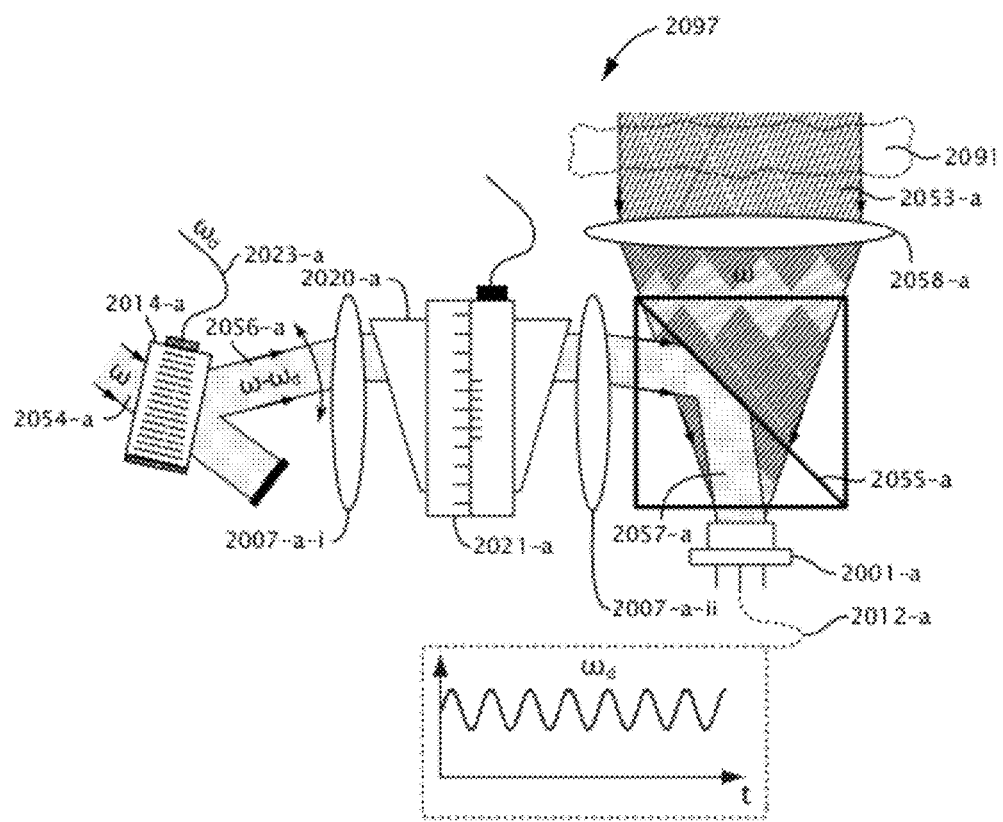
FIG. 20A illustrates a coherent passive sensing system for measuring the complex Fourier components of a wavefront, thereby providing a means for characterizing the object or medium responsible for the wavefront errors.
Figure 20B:
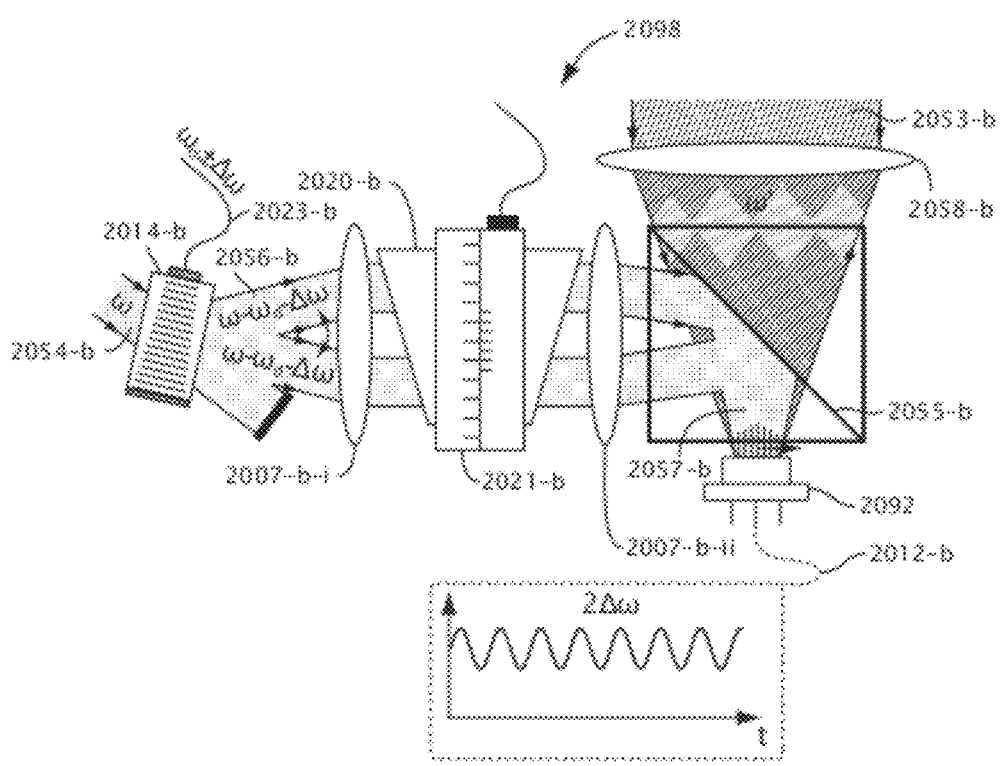
FIG. 20B illustrates an incoherent passive sensing system employing a spatially-modulated structured radiation and a nonlinear detector to measure the spatial Fourier components of an image.
Figure 20C:
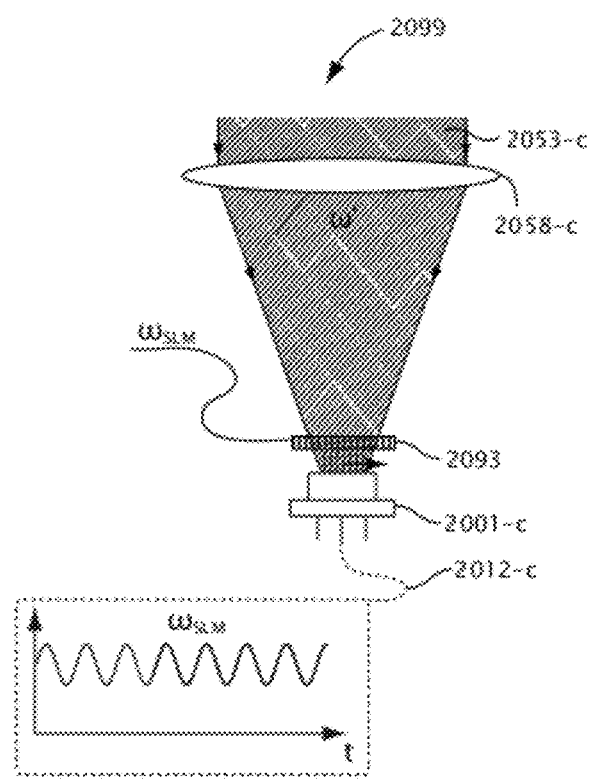
FIG. 20C illustrates an incoherent passive sensing system employing a traveling-wave spatial modulator near the image plane to measure the spatial Fourier components of an image.

Embodiments of the invention may also be used in passive sensing applications where projecting patterns onto a remote target is either impractical or undesirable. FIG. 20A, FIG. 20B, and FIG. 20C show three examples of passive sensing techniques based on the same principles of the microscopy techniques described above. The same signal processing techniques and image reconstruction algorithms used in the microscopy techniques may be applied for reconstructing an image from the Fourier measurements obtained using these methods.

FIG. 20A illustrates the coherent passive sensing system of FIG. 7 used to characterize an object or medium 2092 by measuring the complex Fourier components of a wavefront aberrated by the object or medium. For example, the object 2091 may be a lens with optical aberrations that may be characterized using the system. Alternatively, the medium 2092 may be a turbulent atmospheric layer distorting the image of a remote object illuminated by a laser beam, and the system may be used to measure and compensate for the atmospheric aberrations. This system is denoted generally by reference number 2097 and is one of a variety of possible embodiments within the spirit and scope of this invention that should be apparent to those skilled in the art, including examples provided in the description of FIG. 7.

FIG. 20B illustrates an incoherent passive sensing system employing a spatially-modulated structured radiation and a nonlinear detector to measure the spatial Fourier components of an image. This system is denoted generally by reference number 2098. Merely by way of example, this system may employ an acousto-optic device 2014-$b$ driven by an electrical signal 2023-$b$ to spatially modulate a source radiation 2054-$b$ to generate a diffracted radiation 2056-$b$, which may be rotated using a wavefront rotating element 2021-$b$ such as a prism and directed using lenses 2007-$b$ and a beam splitter 2055-$b$ to form an interference pattern 2057-$b$ on a single-element two-photon detector 2092. At the same time, an image formed by focusing the incoming wavefront 2053-$b$ using a lens 2058-$b$, which may be coherent or incoherent with respect to the structured illumination 2057-$b$, is directed via a beam splitter 2055-$b$ onto the same two-photon detector 2092, which spatially integrates the two-photon response due to the structured illumination and image intensities. Two-photon detection is possible using specially designed semiconductor photodiodes (although these operate in the NIR), which effectively multiply the structured illumination and the image, attaining an analogous spatial heterodyne effect and resulting in an detector signal 2012-$b$ analogous to those obtained in various microscopy embodiments of the invention, so that many of the signal processing techniques and image-reconstruction algorithms of the invention may be directly applied to the two-photon detector signal 2012-$b$ to reconstruct the passively formed image. The structured illumination and the measured wavefront can be of different wavelengths and optical bandwidths. To avoid a strong bias due to two-photon interference of the reference structured illumination alone (which could be much more intense than the incoming wavefront), the wavelengths and semiconductor material can be chosen such that only the combination of a reference photon and a wavefront photon (or the unlikely coincidence of two wavefront photons) is sufficient to overcome the detector bandgap. To attain this bias rejection effect, the reference structured illumination is longer in wavelength than the wavefront being measured.

FIG. 20C illustrates an incoherent passive sensing system employing a traveling-wave spatial modulator near the image plane to measure the spatial Fourier components of an image. In this system denoted generally by reference number 2099, the spatial light modulator 2093 such as a liquid crystal, MEMS, or SAW device is positioned just in front of the single-element detector 2001-$c$, which receives and spatially integrates an image formed by focusing the incoming wavefront 2053-$c$ using a lens 2058-$c$ (although a transmissive system is shown, a reflective design can be easily implemented by placing the spatial light modulator 2093 in a conjugate image plane). Fourier analysis of the intensity distribution at the spatial light modulator 2093 can be accomplished by programming it with a sequence of traveling fringe patterns, or by using a more complex (frequency multiplexed) traveling pattern. In the latter case, the individual complex Fourier components of the image can be recovered by Fourier analysis of the detector signal 2012-$c$, as in frequency-multiplexed microscopy embodiments of the invention. However in contrast to some microscopy embodiments, and as in the other passive sensing embodiments described above, in this case there are no redundant measurements or other frequency multiplexing penalties (since the Fourier analysis is purely two-dimensional).

Figure 21:
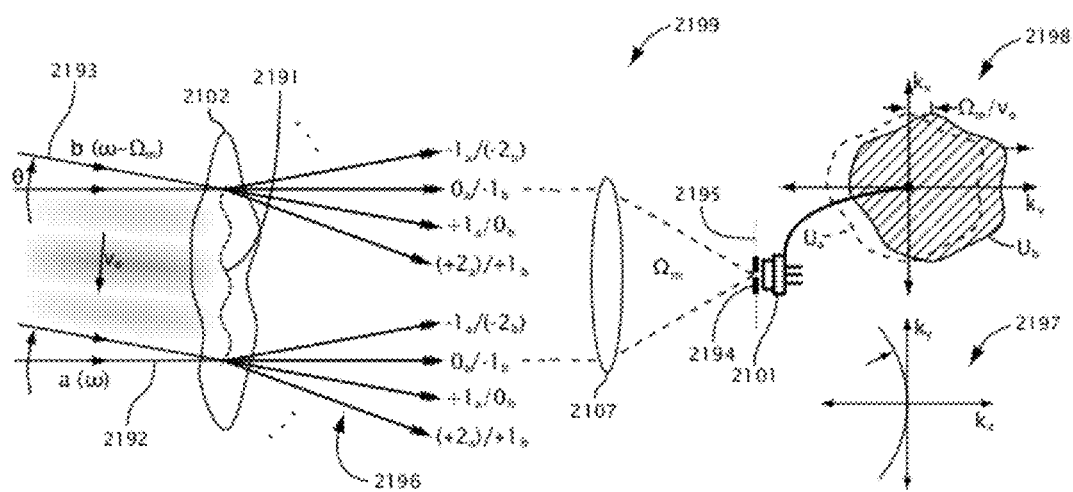
FIG. 21 illustrates measurement of a full complex Fourier slice of a scattering object by using a fixed reference beam aligned with the optical axis and an angle-scanned probe beam that sweeps over both negative and positive angles.

The system illustrated in FIG. 21 and denoted generally by reference number 2199 makes it is possible to measure a full complex Fourier slice of the scattering object 2102 by using a fixed reference beam 2192 aligned with the optical axis and an angle-scanned probe beam 2193 (generated using an acousto-optic Bragg cell, for example) that sweeps over both negative and positive angles. The beams 2192 and 2193 interact with the object 2102 comprised of amplitude or phase sinusoidal components 2191 generating diffracted radiation orders 2196, some of which are collected onto the detector 2101 by lens 2107. In this case, the magnitude and phase of the time-varying intensity signal $i_d(t;\Omega_m)$ (where $\Omega_m$ represents the RF modulation frequency and the corresponding Doppler shift of the scanned beam) at the detector 2101 placed behind a pinhole 2194 in the far-field or in a Fourier plane 2195 of the scattering object 2102 measure the magnitude and phase of the object's Fourier coefficients $U(0,\Omega_m/\upsilon_o)$ along a slice as $\theta$ is scanned, as illustrated in the Fourier-domain in space 2198. The resulting time-varying detector signal may be described as:

$$\tilde{i}_d(t;\Omega_m) \propto |U(0,\Omega_m/\upsilon_o)|\cos(2\Omega_m t + \angle U(0,\Omega_m/\upsilon_o)).$$

Thus, a beat signal at $\Omega_m$ is detected at the center of the Fourier plane whenever a diffracted order 2196 of the scanned beam 2193 aligns with the reference beam 2192. Since the interference pattern illuminating the structure tilts with $\theta$, the Fourier samples are measured along a circle (i.e. a portion of an Ewald sphere) in the $k_y$-$k_z$ plane as illustrated in space 2197, thereby sacrificing the large depth of field of double-sided embodiments. On the other hand, this technique enables simultaneous, quantitative, and unambiguous measurement of both phase and amplitude structures, and enables complex image synthesis through the use of diffraction tomography algorithms, for example. It should be apparent to those skilled in the art that this technique is not limited to sequential scanning of Fourier space and may utilize multiple probe beams or a continuous probing pattern generated by spatially modulating a coherent radiation (using two crossed Bragg cells, for example) and may employ a variety of frequency and wavelength multiplexing schemes, phase calibration techniques, and other methods described in the context of other embodiments of the invention. Moreover, the fixed reference beam 2192 does not need to interact with the object before being received by the detector.

Figure 22:
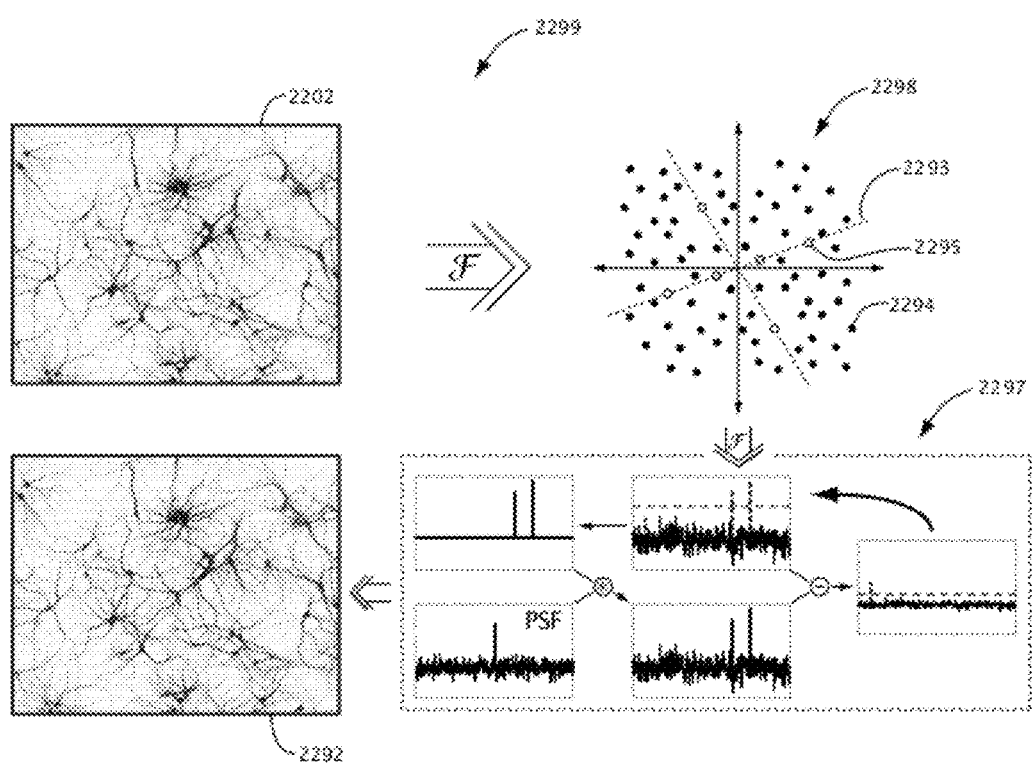
FIG. 22 illustrates the use of random sparse Fourier sampling and compressed sensing algorithms to reduce the number of measurements required to reconstruct a detailed image of an object.

FIG. 22 illustrates the use of random sparse Fourier sampling and compressed sensing algorithms to reduce the number of measurements required to reconstruct a detailed image of an object. Compressive sensing techniques are known to substantially reduce the number of measurements needed to reconstruct some objects by projecting the object information onto a randomly-generated measurement basis. Such compressive sensing concepts can be applied directly to Fourier measurements 2298 obtained with embodiments of the invention. For example, it has been theoretically shown and experimentally demonstrated in the context of MRI that in many cases by measuring randomly-selected Fourier coefficients 2294 of the object 2202 it is possible to greatly reduce the number of measurements required to faithfully reconstruct the image 2292, as in the case of random basis projection. Moreover, other optimal sparse Fourier sampling schemes have also been described in the context of radio astronomy using non-redundant arrays, for example. Regardless of the particular Fourier sampling scheme, constrained iterative techniques (based on L1 norm minimization) similar to the CLEAN algorithm used in radio astronomy and depicted schematically in space 2297, for example, can be used to recover the image 2292 from the sparse set of Fourier coefficients 2298. Since in embodiments of the invention the set of Fourier coefficients 2295 measured along any given Fourier slice 2293 is unrestricted (there is no scanning time penalty for jumping between spatial frequencies), sparse Fourier sampling can be used to reduce measurement time without sacrificing image quality. Moreover, with non-mechanical Fourier scanning (e.g. using crossed Bragg cells as described above) "random-access" Fourier sampling can be extended to 2D and even 3D. Thus, embodiments of the invention may provide a very flexible programmable platform for single-pixel compressive sensing in the Fourier domain.

Figure 23:
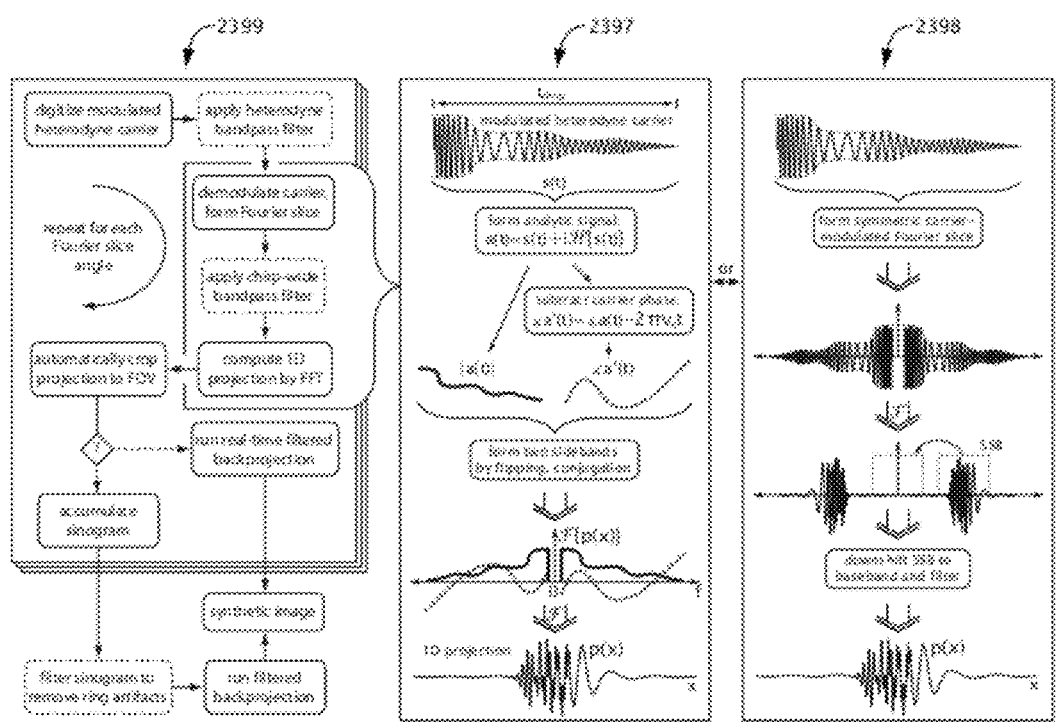
FIG. 23 illustrates data processing flow for various embodiments of the invention based on chirped heterodyne measurements.

FIG. 23 illustrates data processing flow for various embodiments of the invention based on chirped heterodyne measurements. In some embodiments an electronic heterodyne process results in a modulated single-tone carrier centered at the heterodyne frequency. To recover the complex Fourier slice from the digitized signal, the envelope and phase of the carrier signal that correspond to the magnitude and phase of the Fourier slice respectively are demodulated, as illustrated by the steps in the overall signal processing flow 2399. This may be accomplished by employing a Hilbert transform to convert the digitized signal into its analytic representation and subtracting the linear phase due to the carrier. The resulting complex signal corresponds to the demodulated single sideband of the Fourier slice covered by the chirp. The full Fourier slice may then synthesized by reflecting this signal about DC (while conjugating the phase) and setting the missing frequencies in the narrow DC region to zero. The steps of carrier demodulation using a Hilbert transform are illustrated in box 2397. Instead of using the Hilbert transform, the one-dimensional projection may be recovered directly by flipping the digitized modulated carrier waveform about DC (and filling in the zeroes near DC) to generate a double-sideband modulated Fourier slice, Fourier transforming the result, downshifting to baseband to remove the heterodyne carrier, applying a 50 kHz digital bandpass filter centered at BC, and converting from frequency to temporal (or equivalently, spatial) coordinates. This process is illustrated in box 2398.

In addition to the demodulation scheme, in some embodiments the processing flow 2399 may include: (1) optional digital bandpass filtering of the heterodyne signal; (2) automatic cropping of the one-dimensional projections to increase processing speed and reduce memory requirements; (3) real-time filtered backprojection, in which reconstruction takes shape as the data are acquired slice by slice; and (4) sinogram filtering to reduce ring artifacts. Since ring artifacts map to columns in the sinogram, they may be dealt with in the sinogram domain. In this scheme, the sinogram is collapsed to a one-dimensional array by summing across all the rows. This operation averages out the signal, but retains common-mode horizontal variations in the sinogram rows that map to radial variations in the reconstructed image. The resulting collapsed array is then smeared vertically and subtracted from the original sinogram. Although this process works well in reducing the ring artifacts, it can also inadvertently remove signals near the center of rotation of the backprojected image and thus should be used with caution.

Figure 24:
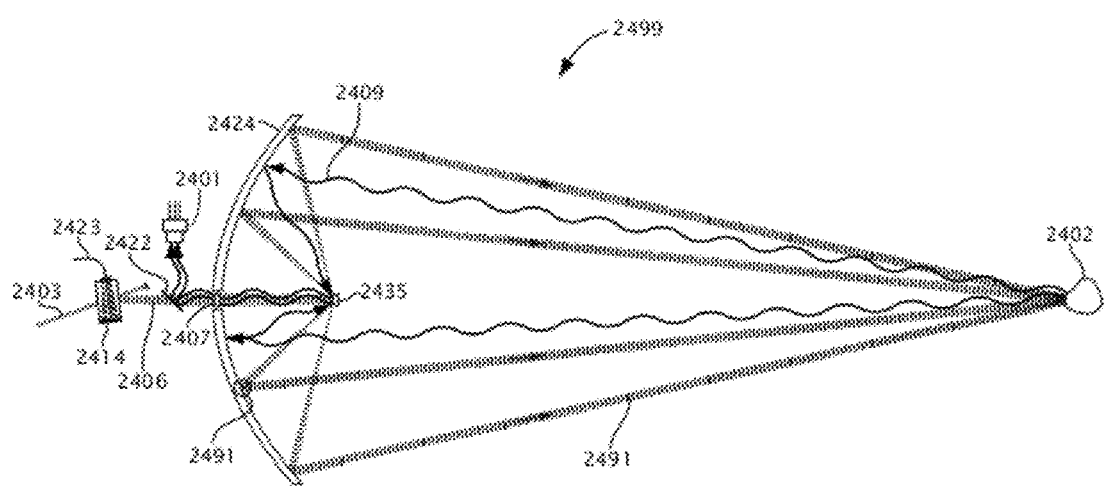
FIG. 24 illustrates a system for measuring remote objects with microscopic resolution using a large phase-compensated reflector.

FIG. 24 illustrates a system, denoted generally by reference number 2499, for measuring remote objects with microscopic resolution using a large phase-compensated reflector. An aspect of some embodiments of the invention is the ability to electronically correct coarse phase errors in the pupil function of the illumination optics as illustrated in FIG. 3A and described elsewhere in this document. This makes it possible to use a low-precision large reflecting dish 2424 (e.g. an ellipsoid) to project thin "pencil beams" 2491 that interfere at a remote object 2402 which may be several meters away, for example. In the illustrated embodiment, a lens 2407 and a small secondary mirror 2435 (e.g. a paraboloid) are used to magnify the angles of the radiation 2406 diffracted by a Bragg cell 2414 illuminated by radiation 2403, such that the Bragg cell effectively scans the pencil beams 2491 across the dish 2424 generating dynamic patterns 2408 of different frequencies at the object 2402. These dynamic patterns may be rotated with respect to the object using a prism or alternatively multi-dimensional dynamic patterns may be generated using two crossed Bragg cells as in other embodiments, for example. As long as the reflector surface 2424 is of optical quality in the small region 2492 illuminated by a pencil beam, coarser linear or piston phase errors in the dish can be compensated by phase-shifting the Bragg cell drive signal 2423 components or by applying corrective phases during Fourier synthesis. The phase errors may be estimated using phase closure techniques as described above, for example. This enables diffraction-limited remote microscopy that would normally require a precision lens as large as the reflector dish 2424, while providing a much larger depth of field. The large reflector may be machined from metal with a honeycomb or drilled substrate to make it lightweight, or even deployed as a mosaic of mirrors. The same large dish may also be used to efficiently collect light 2409 from the object and direct it via a backend beam splitter 2422 onto a sensitive single-element detector 2401. The detector signal may then be processed to reconstruct the image of the remote object 2402 as in other embodiments of the invention. The large collecting aperture of the dish may be especially well suited for efficiently collecting the weak response radiation in remote fluorescence microscopy.

Figure 25:
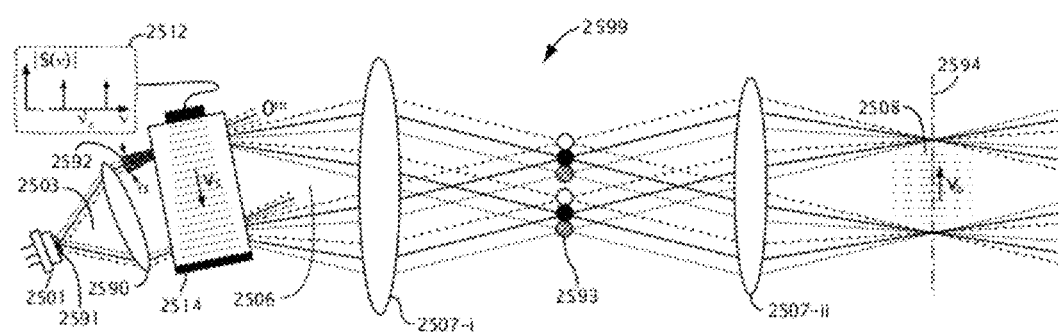
FIG. 25 illustrates a system that employs a spatially incoherent source to limit the depth of field and increase axial resolution.

FIG. 25 illustrates a system, denoted generally by reference number 2599, that employs a spatially incoherent source to limit the depth of field and increase axial resolution. An extended source 2501 such as an LED may be treated as a group of small mutually-incoherent shifted radiation sources 2591. The resulting radiation 2503 is collimated and directed by a lens 2590 onto a Bragg cell 2514 such that radiation from each shifted source arrives at the Bragg cell at a slightly different incidence angle. Radiation 2506 diffracted by the Bragg cell driven by a pair of tones 2512 is focused by lens 2507-*i* to form images 2593 of the small radiators in an intermediate Fourier plane and is recollimated by lens 2507-*ii* to produce an illumination pattern 2508 at the object plane 2594. This illumination pattern can be understood as an incoherent sum of slightly tilted interference patterns of the same spatial frequency. The tilted patterns combine in-phase near the object plane 2594, but increasingly out-of-phase away from it, so that the contrast of the incoherently-combined interference patterns is high near the object plane but falls with defocus resulting in a depth-apodized fringe visibility and a reduced depth of field. The reduction of fringe visibility with depth due to limited spatial coherence depends on the spatial frequency of the projected pattern (lower frequencies wash out more gradually with depth than higher ones). The dependence of the axial extent of the combined interference pattern on the spatial coherence of the illumination can be used to attain axial sectioning in various embodiments of the invention since away from the object plane the illumination is only weakly modulated and contributes little to the AC detector signal.

In discussing the effects of partial spatial coherence, it is important to take into account the acceptance angle 2592 of the Bragg cell, which characterizes the dependence of diffraction efficiency on the incidence angle. Since collimated light from each resolvable independent radiator 2591 in the extended source 2501 arrives at the Bragg cell at a slightly different angle, the limited acceptance angle of the Bragg cell creates a spatial filter, potentially increasing the spatial coherence depending on the size of the source and the focal length of the collimating lens. For a typical $TeO_2$ Bragg cell, the acceptance angle may be as much as several degrees (depending on the bandshape flatness requirements). Thus, a 500 µm-wide LED may need to be collimated using a lens with a focal length of ~15 mm or greater in order to not exceed a 2° Bragg cell acceptance angle, for example.

Figure 26:
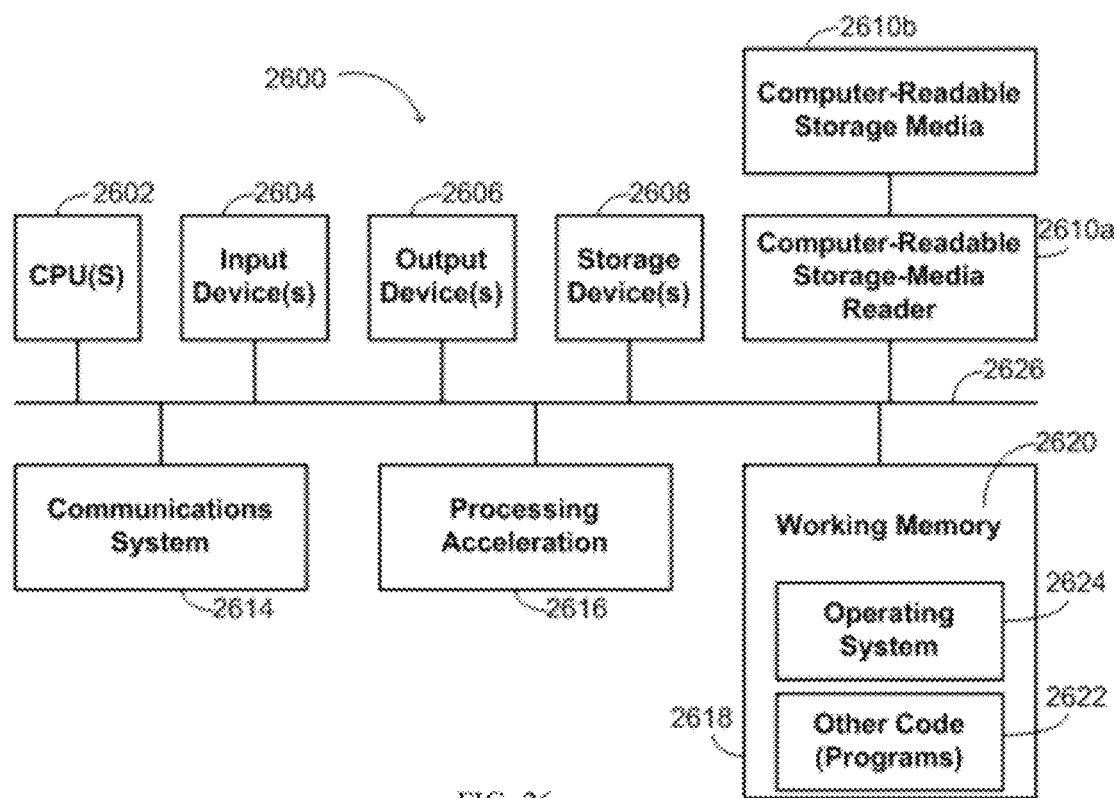
FIG. 26 is a schematic illustration of a computational device that may be used in part to implement embodiments of Fourier domain sensing systems, apparatuses, and methods, in accordance with various embodiments.

The methods, apparatuses, and systems described in connection with the various systems and methods described above may be implemented in part by using a computational device 2600 such as shown schematically in FIG. 26, which broadly illustrates how individual system elements may be implemented in a separated or more integrated manner. The device 2600 is shown comprised of hardware elements that may be electrically coupled via bus 2626. The hardware elements may include a processor 2602, an input device 2604, an output device 2606, a storage device 2608, a computer-readable storage media reader 2610a, a communications system 2614, a processing acceleration unit 2616 such as a DSP or special-purpose processor, and a memory 2618. The computer-readable storage media reader 2610a may be further connected to a computer-readable storage medium 2610b, the combination comprehensively representing remote, local, fixed, and/or removable storage devices plus storage media for temporarily and/or more permanently containing computer-readable information. The communications system 2614 may comprise a wired, wireless, modem, and/or other type of interfacing connection and permits data to be collected from the Fourier domain sensing systems. In some instances, such data collection may be performed in real time by the communications system. In some instances, one or more characteristics of the measured Fourier components may be computed from such collected data by using a lookup table stored within the memory 2618, storage device 2608, on computer readable storage media 2610, and/or within storage elements embedded within the processor 2602 and/or processor acceleration unit 2616.

The device 2600 may also include software elements, shown as being currently located within working memory 2620, which may include an operating system 2624 and other code 2622, such as a program designed to implement methods of the invention. Merely by way of example, device 2600 may include processing code that may include instructions to determine one or more characteristics of sinusoidal Fourier components of the object based on a time-varying signal, merely by way of example. Processing code may also be included to reconstruct, synthesize, display, and/or analyze images of the object. Code may also be included to control and/or to implement embodiments of different Fourier domain sensing systems. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

It should be noted that the methods, systems, and devices discussed above are intended merely to be examples. Various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Many of the elements are intended as illustrative examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "memory" or "memory unit" may represent one or more devices for storing data, including read-only memory (ROM), random access memory (RAM), magnetic RAM, core memory, magnetic disk storage mediums, optical storage mediums, flash memory devices, or other computer-readable mediums for storing information. The term "computer-readable medium" includes, but is not limited to, portable or fixed storage devices, optical storage devices, wireless channels, a sim card, other smart cards, and various other mediums capable of storing, containing, or carrying instructions or data.

Furthermore, embodiments may be implemented by hardware, software, firmware, middleware, microcode, hardware description languages, or any combination thereof. When implemented in software, firmware, middleware, or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents may be used without departing from the spirit of the invention. By way of example, several such variations are set forth here, but this identification of potential variations is not intended to be exhaustive, and other variations will be evident for those of skill in the art.

For instance, while the optics have been described for particular types of systems in the illustrative embodiments, the principles of the invention may more generally be implemented with reflective optics, transmissive optics, or combinations thereof. While Bragg cells have been used to illustrate one technique for enabling spatial modulation, it can more generally use any of a variety of technologies that include AO, SAW, LCD, MEMS, and others. Spatial modulators may be one-dimensional or two-dimensional, and may incorporate different spatial-modulator technologies and arrangements. Dispersive elements may include gratings, diffractive optical elements, holograms, prisms, grisms, AO devices, programmable MEMS devices, and the like. In broadband schemes, radiation may be spatially coherent or not, and certain embodiments may be implemented regardless of spatial or temporal coherence of the illumination (e.g., compressive sensing, etc.). Two-dimensional and three-dimensional Fourier samples can be measured by mechanically rotating and/or tilting illumination produced by a one-dimensional spatial modulator or by generating multi-dimensional patterns using a two-dimensional spatial modulator without requiring mechanical rotation. Object response may be coherent (e.g. scattered) or incoherent (e.g. fluoresced) in different embodiments.

The arrangements illustrated in the drawings and described above are simple so that the principles of operation will be evident, but it will be appreciated that other systems may be implemented in a more complex fashion, such as by involving a greater number of lenses than shown and/or by involving additional conjugate optical planes. In some embodiments, Fourier sample acquisition may be sequential, RF frequency-multiplexed, and/or wavelength-multiplexed. In wavelength-multiplexed embodiments, radiation from the object may be spectrally dispersed onto an array of detectors, may illuminate an array of filtered detectors, or, in some cases, may be detected using a single detector and a sequence of spectral filters. Although a single spatially integrating detector has been described above for most embodiments, it will be understood that parallelized embodiments using multiple detectors to look at different parts of the object, different spectral bands, different polarizations, etc. are also within the intended scope of the invention, and may be used in various embodiments where only a single detector has been described.

In some illustrative embodiments, only a pair of interfering beams has been shown (sequential Fourier sampling), but the same principles typically also apply when many beams or when a continuous spatially modulated wavefront is diffracted. Such alternative embodiments are also within the intended scope of the invention. While the above description at times refers to a given illumination spatial frequency measuring a single Fourier component, it will be appreciated that it is alternatively possible to measure multiple harmonic Fourier components at once when the illumination is sufficiently strong and the response is nonlinear. Even without explicit mention of such variations, the descriptions apply equally well to such a nonlinear response as they do to a linear response.

In addition, the above elements may merely be a component of a larger system, wherein other rules may take precedence over or otherwise modify the application of the invention. Also, a number of steps may be undertaken before, during, or after the above elements are considered.

Accordingly, the above description should not be taken as limiting the scope of the invention, which is defined in the following claims.

What is claimed is:

1. A method of sensing an object, the method comprising:
spatially modulating a first radiation to generate a structured second radiation;
illuminating the object with the structured second radiation such that the object produces a third radiation in response, wherein, apart from any spatially dependent delay, the third radiation has a time variation that is substantially spatially independent;
detecting, with a single-element detector, a portion of the third radiation from a plurality of locations on the object substantially simultaneously; and
estimating at least one characteristic of one or more sinusoidal spatial Fourier-transform components of the object from a time-varying signal from the detected portion of the third radiation.

2. The method recited in claim 1 wherein:
spatially modulating the first radiation comprises propagating a traveling modulation pattern along a direction;
diffracting a plane-wave component of the second radiation; and
imparting a Doppler frequency shift on the plane-wave component.

3. The method recited in claim 2 wherein:
the second radiation comprises a plurality of plane-wave components;
each distinct pair of the plane-wave components interferes to produce a traveling sinusoidal excitation pattern component probing one or more harmonic spatial Fourier-transform components of the object and contributing a time-varying detector signal comprising one or more frequencies corresponding to an integer multiple of a temporal frequency difference of the each distinct pair of plane-wave components and having zero or nonzero frequency offset.

4. The method recited in claim 3 wherein:
the traveling modulation pattern is produced using one or more acousto-optic devices comprising at least one of a Bragg cell or a surface-acoustic-wave optical modulator; and
each of the acousto-optic devices is controlled with an electrical drive signal, each frequency component of the electrical drive signal or an intermodulation thereof imparting a harmonic Doppler frequency shift to one of the plane-wave components of the second radiation.

5. The method recited in claim 4 wherein:
spatially modulating the first radiation comprises spatially modulating the first radiation along a plurality of non-parallel directions;
the acousto-optic devices comprise at least one of a multi-dimensional acousto-optic device or a plurality of non-collinear acousto-optic devices arranged in tandem in close proximity to each other or in conjugate optical planes; and
the drive signals comprise an array of frequencies, wherein at least one pair of frequencies results in a distinct tone in the time-varying detector signal that measures a distinct component of a three-dimensional Fourier transform of the object.

6. The method recited in claim 4 wherein the electrical drive signal comprises one or more electrical drive signals comprising a non-redundant array of frequencies.

7. The method recited in claim 3 wherein:
the second radiation comprises a plurality of plane-wave components; and
a difference between temporal frequencies of each pair of plane-wave components is substantially distinct from temporal frequency differences of other pairs of plane-wave components that produce distinct sinusoidal excitation patterns.

8. The method recited in claim 3 wherein estimating the characteristic of the sinusoidal spatial Fourier-transform components of the object comprises obtaining substantially simultaneous measurements of one or more distinct spatial Fourier-transform components of the object from the signal by Fourier analysis.

9. The method recited in claim 3 wherein:
a response by the object to the second radiation is nonlinear; and
a portion of the time-varying signal due to a sinusoidal excitation pattern component comprises harmonic temporal frequencies measuring harmonic spatial Fourier-transform components.

10. The method recited in claim 9 wherein the response is due to saturable fluorescence.

11. The method recited in claim 9 wherein the response is due to depletion of fluorescence using an auxiliary depletion illumination pattern traveling substantially in unison with the traveling sinusoidal excitation pattern but operating at a substantially distinct wavelength.

12. The method recited in claim 9 wherein the response is coherent.

13. The method recited in claim 1 wherein the second radiation has a spectral distribution, the method further comprising controlling a width of the spectral distribution to set a depth of field of the sensing.

14. The method recited in claim 13 further comprising controlling a group delay dispersion of the first radiation to set a focal plane of the sensing.

15. The method recited in claim 1 wherein the first and second radiations have a spectral distribution, the method further comprising angularly spectrally dispersing wavelengths of the first radiation to maintain an extended depth of field, wherein depth of field and resolution are substantially decoupled.

16. The method recited in claim 1 wherein the first radiation has a partial spatial coherence.

17. The method recited in claim 16 further comprising controlling the partial spatial coherence of the first radiation to set a depth of field of the sensing.

18. The method recited in claim 1 wherein:
the second radiation has a spectral distribution; and
as a result of a limited coherence of the first radiation, portions of the time-varying signal due to illumination that is scattered at least once before impinging on the object are suppressed relative to portions of the time-varying signal due to illumination not thus scattered, resulting in increased measurement contrast and extended measurement depth within or behind a scattering medium.

19. The method recited in claim 18 wherein
the scattering medium comprises biological tissue; and
the third radiation is fluoresced by a component of the biological tissue in response to the illumination.

20. The method recited in claim 1 wherein the third radiation is due to at least one of multiphoton fluorescence, harmonic generation, coherent nonlinear frequency mixing, or Raman Scattering.

21. The method recited in claim 20 further comprising illuminating the object with a fourth radiation, wherein:
the fourth radiation comprises a counter-propagating pulsed radiation having a different spectrum from the second radiation;
the second radiation is pulsed; and
the third radiation is spectrally filtered,
whereby the time-varying signal is detected only when the second and fourth radiation pulses overlap in time and space to produce emission with a spectrum distinct from the spectra of the second and fourth radiations.

22. The method recited in claim 21 further comprising adjusting a relative timing of pulses of the second and fourth radiations to control an axial location of overlap of such pulses, thereby providing axial sectioning.

23. The method recited in claim 1 wherein:
the second radiation passes through a high-index medium having a higher index of refraction than a sample medium and forms an evanescent field pattern extending into the sample medium at an interface between the high-index medium and the sample medium; and
the object is located substantially adjacent to the interface such that it is at least partially within the evanescent field pattern.

24. The method recited in claim 1 wherein the sinusoidal spatial Fourier-transform components of the object have a substantially sparse and approximately random distribution in the Fourier domain, the method further comprising applying a compressed sensing algorithm utilizing a minimization of a norm to synthesize a one-dimensional or multi-dimensional image or a transform of such image.

25. The method recited in claim 1 further comprising compensating for errors in a wavefront of the structured second radiation while or after estimating the characteristic.

26. The method recited in claim 25 wherein:
the characteristic comprises phase; and
compensating for errors in the wavefront of the structured second radiation comprises forming closure phases from the estimated Fourier phases.

27. The method recited in claim 25 wherein:
the single-element detector comprises one or more detectors;
the second and third radiations each have a spectral distribution;
detecting the portion of the third radiation comprises separately sensing distinct wavelength ranges, at least two of such separate sensings detecting a portion of the third radiation due to the same Fourier component of the object; and
compensating for errors in the wavefront of the structured second radiation comprises using signals from the separate sensings.

28. The method recited in claim 1 wherein the object is located at a distance, the method further comprising:
using an optical surface with coarse phase errors to illuminate the object with the structured second radiation; and
compensating the coarse phase errors of the optical surface by making adjustments to at least one of the phase of the sinusoidal components of the structured illumination or the phase of the measured spatial Fourier-transform components of the object.

29. The method recited in claim 1 wherein the time-varying signal has a carrier frequency, the method further comprising demodulating the time-varying signal from the carrier by applying a Hilbert transform to obtain an analytic signal and subtracting a carrier phase function from the analytic signal.

30. The method recited in claim 1 wherein the time-varying signal has a carrier frequency, the method further comprising demodulating the time-varying signal from the carrier by down-converting and bandpass-filtering a Fourier transform of the detected signal.

31. The method recited in claim 1 wherein:
the single-element detector comprises a plurality of detectors, each of the detectors having a distinct wavelength range; and the second radiation has a centrosymmetric position-dependent wavelength distribution substantially near a Fourier-transform optical plane of the spatial modulation.

32. A method for measuring one or more sinusoidal spatial Fourier-transform components of an object, the method comprising:
    illuminating the object with a first probing radiation comprising one or more plane-wave components having distinct directions of propagation, wherein the object produces a second radiation in response to such illuminating;
    imparting a distinct frequency shift on each of the probing radiation components;
    detecting, with a single-element detector, a third reference radiation substantially coherent with respect to the first probing radiation and a portion of the second radiation from a plurality of locations on the object substantially simultaneously; and
    estimating at least one characteristic of the one or more sinusoidal spatial Fourier-transform components of the object based on a time-varying signal from the detected second and third radiations.

33. The method recited in claim 32 wherein:
    the object comprises phase structure; and
    a portion of the second radiation is due to coherent scattering of the first radiation by the phase structure.

34. The method recited in claim 32 wherein imparting the distinct frequency shift on the first radiation components comprises utilizing at least one of a one-dimensional acousto-optic Bragg cell, a multi-dimensional acousto-optic Bragg cell, a surface-acoustic-wave optical modulator, a programmable grating device, a liquid crystal array, or a digital micromirror device.

35. A method for measuring one or more plane-wave components of a first radiation, the method comprising:
    illuminating a single-element detector with the first radiation and with a second radiation substantially coherent with respect to the first radiation, the second radiation comprising one or more plane-wave components having distinct directions of propagation;
    imparting a distinct frequency shift on each of the second radiation components;
    detecting the first and second radiations with the detector substantially simultaneously; and
    estimating at least one of amplitude, phase, or direction of propagation of the one or more plane-wave components of the first radiation based on a time-varying signal due to the detected radiations.

36. The method recited in claim 35 wherein imparting the distinct frequency shift on the second radiation components utilizes at least one of a one-dimensional acousto-optic Bragg cell, a multi-dimensional acousto-optic Bragg cell, a surface-acoustic-wave optical modulator, a programmable grating device, a liquid crystal array, or a digital micromirror device.

37. The method recited in claim 35 wherein the first radiation is reflected or transmitted by an object, the method further comprising estimating a characteristic of the object from measurements of the one or more plane-wave components.

38. A method for measuring one or more sinusoidal spatial Fourier-transform components of a portion of an image formed by a first radiation, the method comprising:
    generating a structured third radiation by spatially modulating a second radiation;
    illuminating a single-element multiphoton detector with the structured third radiation and with the first-radiation image portion;
    detecting the first and third radiations with the multiphoton detector substantially simultaneously; and
    estimating a characteristic of the one or more sinusoidal spatial Fourier-transform components of the portion of the image based on a time-varying signal due to the detected radiations.

39. The method recited in claim 38 wherein spatially modulating the second radiation utilizes at least one of a one-dimensional acousto-optic Bragg cell, a multi-dimensional acousto-optic Bragg cell, a surface-acoustic-wave optical modulator, a programmable grating device, a liquid crystal array, or a digital micromirror device.

40. A method for measuring a sinusoidal spatial Fourier-transform component of a portion of an image formed by a first radiation, the method comprising:
    spatially modulating an amplitude of the portion of the image with a traveling modulation pattern to form a structured second radiation;
    detecting a portion of the structured second radiation from a plurality of locations on the image substantially simultaneously; and
    estimating a characteristic of the sinusoidal spatial Fourier transform component of the portion of the image based on a time-varying signal due to the detected radiation.

* * * * *